(12) United States Patent
Cunningham et al.

(10) Patent No.: US 6,210,863 B1
(45) Date of Patent: Apr. 3, 2001

(54) BORATE COINITIATORS FOR PHOTOPOLYMERIZATION

(75) Inventors: Allan Francis Cunningham, Marly (CH); Martin Kunz, Efringen-Kirchen (DE); Hisatoshi Kura, Hyogo (JP)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 09/314,391

(22) Filed: May 19, 1999

Related U.S. Application Data

(62) Division of application No. 08/755,380, filed on Nov. 21, 1996, now Pat. No. 5,952,152.

(30) Foreign Application Priority Data

Nov. 24, 1995  (CH) .................................................. 3342/95

(51) Int. Cl.[7] .................................................. G03F 7/027
(52) U.S. Cl. ........................ 430/281.1; 430/914; 568/1; 568/6; 522/6
(58) Field of Search ........................ 522/6, 7; 526/196; 568/1, 6; 430/281.1

(56) References Cited

U.S. PATENT DOCUMENTS

| 4,772,530 | 9/1988 | Gottschalk et al. ................. 430/138 |
| 4,772,541 | 9/1988 | Gottschalk et al. ................. 430/339 |
| 4,954,414 | 9/1990 | Adair et al. ........................... 430/138 |
| 4,971,891 | 11/1990 | Kawamura et al. ................. 430/278 |
| 5,055,372 | 10/1991 | Shanklin et al. ..................... 430/138 |
| 5,151,520 | 9/1992 | Gottschalk et al. ................. 548/110 |
| 5,340,898 | * 8/1994 | Cavezzan et al. ..................... 528/19 |
| 5,475,119 | 12/1995 | Baur et al. ............................ 548/570 |
| 5,563,016 | 10/1996 | Baur et al. ............................ 430/110 |

FOREIGN PATENT DOCUMENTS

| 0542286 | 5/1993 | (EP) . |
| 0543022 | 5/1993 | (EP) . |
| 0548826 | 6/1993 | (EP) . |
| 0555058 | 8/1993 | (EP) . |
| 0609452 | 1/1994 | (EP) . |
| 3834960 | 10/1988 | (GB) . |

OTHER PUBLICATIONS

Caplus abstract AN 1991:122495.*
Caplus abstract AN 1981:65778.*
Chemical Abstract—120:298230f of JP Hei 5255347.

Proceedings of the Radtech, 98 Conference, Apr. 19–22 in Chicago, IL 1998 p. 215–226 K. Feng, et al.

Journal of Chemical Society, Perkin II, p. 1225–1232 (1978).

Journal of Organic Chemistry, vol. 29, pp. 1971–1976 (1964) R. Damico.

* cited by examiner

*Primary Examiner*—Janet Baxter
*Assistant Examiner*—Rosemary Ashton
(74) *Attorney, Agent, or Firm*—Luther A. R. Hall

(57) ABSTRACT

Compounds of the formula I or I'

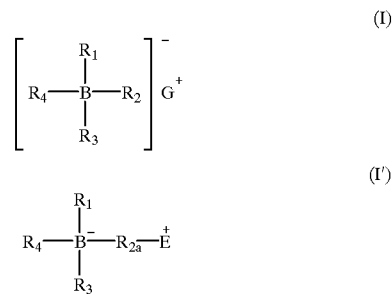

in which $R_1$ and $R_2$ independently of one another, for example, are an aromatic hydrocarbon, with the proviso that the aromatic hydrocarbon radical is substituted in at least one o-position, or $R_1$ and $R_2$, for example, independently of one another are $C_1$–$C_{20}$alkyl, which is substituted by $R_9R_{10}R_{11}Si$; $R_{2a}$ is, for example, a divalent aromatic hydrocarbon radical; $R_3$ is $C_1$–$C_{20}$alkyl which is substituted by $R_9R_{10}R_{11}Si$ or is an aromatic hydrocarbon; $R_4$ is, for example, $C_1$–$C_{20}$alkyl, $C_3$–$C_{12}$cycloalkyl or phenyl-$C_1$–$C_6$alkyl; E is $R_{14}R_{15}R_{16}P$ or $R_8R_{8a}R_7N$; $R_7$, $R_8$ and $R_{8a}$ and $R_9$, $R_{10}$ and $R_{11}$ independently of one another are, for example, $C_1$–$C_{12}$alkyl; $R_{14}$, $R_{15}$ and $R_{16}$ independently of one another are substituted phenyl and G is a radical which is able to form positive ions, with the proviso that, if $R_1$, $R_2$ and $R_3$ are 2,4,6-trimethylphenyl, $R_4$ is not $C_2$–$C_{20}$alkyl or $C_2$–$C_8$alkenyl, are suitable for use as particularly reactive photoinitiators.

15 Claims, No Drawings

BORATE COINITIATORS FOR PHOTOPOLYMERIZATION

This is a divisional of application Ser. No. 08/755,380, filed on Nov. 21, 1996, now U.S. Pat. No. 5,952,152, issued on Sep. 14, 1999.

The invention relates to highly reactive borate photoinitiator compounds, to compositions comprising these compounds, and to the use of the compounds.

The use of borates as photoinitiators in combination with coinitiators is known in the prior art. For example, U.S. Pat. Nos. 4,772,530, 4,772,541 and 5,151,520 disclose triaryl alkyl borate anions with cationic dyes, for example cyanines, rhodamines, etc., as counterions. These compounds are employed as photoinitiators. In U.S. Pat. No. 4,954,414, cationic transition metal complexes are used together with triaryl alkyl borate anions in photopolymerizable compositions. From U.S. Pat. No. 5,055,372 it is also known to use quaternary ammonium compounds, for example tetramethylammonium, pyridinium, cetylpyridinium, etc., as cationic counterions to the triaryl alkyl borate. In this publication, the borates are employed in association with aromatic ketone initiator compounds as coinitiators in photocurable materials. In EP-A-555 058 and JP-A Hei 5 255347, borates, including trimesityl butyl borate among others, are used as coinitiators for (oxo) sulfonium complexes.

For the extensive range of applications of photoinitiators, there is a requirement in the industry for stable reactive compounds.

It has surprisingly now been found that monoborate compounds which are ortho-substituted on at least two aryl radicals possess these properties to a high degree. The invention therefore provides compounds of the formulae I and I'

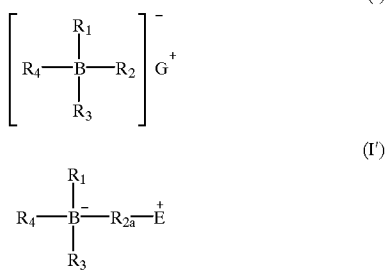

in which $R_1$ and $R_2$ independently of one another are phenyl or another aromatic hydrocarbon, with or without any heteroatom, which radicals are unsubstituted or are substituted 1–5 times by $C_1$–$C_{20}$alkyl, $C_2$–$C_{20}$alkyl which is interrupted by one or more radicals O, $S(O)_p$ or $NR_5$, or are substituted by $OR_6$, $R_6S(O)_p$, $R_6S(O)_2O$, $R_7R_8N$, $R_6OC(O)$, $R_7R_8NC(O)$, $R_9C(O)$, $R_9R_{10}R_{11}Si$, $R_9R_{10}R_{11}Sn$, $R_{12}R_{13}B$, halogen, $R_9R_{10}P(O)_q$, and/or CN, with the proviso that the phenyl radical or the other aromatic hydrocarbon radicals are substituted in at least one o-position, or $R_1$ and $R_2$ independently of one another are $C_1$–$C_{20}$alkyl which is substituted by $R_9R_{10}R_{11}Si$, or the radicals $R_1$ and $R_2$ form bridges to produce structures of the formula II, IIa or IIb

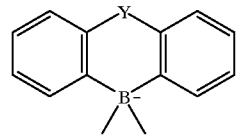

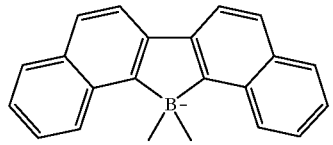

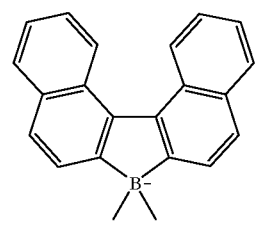

where the aromatic rings in the formulae II, IIa or IIb are unsubstituted or are substituted by $C_1$–$C_{20}$alkyl, $C_2$–$C_{20}$alkyl which is interrupted by one or more radicals O, $S(O)_p$ or $NR_5$ or are substituted by $OR_6$, $R_6S(O)_p$, $R_6S(O)_2O$, $R_7R_8N$, $R_6OC(O)$, $R_7R_8NC(O)$, $R_9C(O)$, $R_9R_{10}R_{11}Si$, $R_9R_{10}R_{11}Sn$, halogen, $R_9R_{10}P(O)_q$ and/or $R_{12}R_{13}B$;

$R_{2a}$ is phenylene or another divalent aromatic hydrocarbon, with or without any heteroatom, which radicals are unsubstituted or are substituted 1–5 times by $C_1$–$C_{20}$alkyl, $C_2$–$C_{20}$alkyl which is interrupted by one or more radicals O, $S(O)_p$ or $NR_5$, or are substituted by $OR_6$, $R_6S(O)_p$, $R_6S(O)_2O$, $R_7R_8N$, $R_6OC(O)$, $R_7R_8NC(O)$, $R_9C(O)$, $R_9R_{10}R_{11}Si$, $R_9R_{10}R_{11}Sn$, $R_{12}R_{13}B$, halogen, $R_9R_{10}P(O)_q$, and/or CN, or $R_{2a}$ is phenyl-$C_1$–$C_6$alkylene;

$R_3$ is $C_1$–$C_{20}$alkyl which is substituted by $R_9R_{10}R_{11}Si$, or is phenyl or another aromatic hydrocarbon, with or without any heteroatom, where the phenyl radical or the other aromatic hydrocarbon radicals are unsubstituted or are substituted 1–5 times by $C_1$–$C_{20}$alkyl, $C_2$–$C_{20}$alkyl which is interrupted by one or more radicals O, $S(O)_p$ or $NR_5$, or are substituted by $OR_6$, $R_6S(O)_p$, $R_6S(O)_2O$, $R_7R_8N$, $R_6OC(O)$, $R_7R_8NC(O)$, $R_9C(O)$, $R_9R_{10}R_{11}Si$, $R_9R_{10}R_{11}Sn$, $R_{12}R_{13}B$, halogen, $R_9R_{10}P(O)_q$, and/or CN;

$R_4$ is phenyl, another aromatic hydrocarbon, $C_1$–$C_{20}$alkyl, $C_2$–$C_{20}$alkyl which is interrupted by one or more radicals O, $S(O)_p$ or $NR_5$, or is $C_3$–$C_{12}$cycloalkyl, $C_2$–$C_8$alkenyl, phenyl-$C_1$–$C_6$alkyl or naphthyl-$C_1$–$C_3$alkyl, where the radicals phenyl, another aromatic hydrocarbon, $C_1$–$C_{20}$alkyl, $C_3$–$C_{12}$cycloalkyl, $C_2$–$C_8$alkenyl, phenyl-$C_1$–$C_6$alkyl or naphthyl-$C_1$–$C_3$alkyl are unsubstituted or are substituted by $OR_6$, $R_6S(O)_p$, $R_6S(O)_2O$, $R_7R_8N$, $R_6O(O)$, $R_7R_8NC(O)$, $R_9C(O)$, $R_9R_{10}R_{11}Si$, $R_9R_{10}R_{11}Sn$, $R_{12}R_{13}B$, halogen, $R_9R_{10}P(O)_q$, and/or CN;

E is $R_{14}R_{15}R_{16}P$, $R_6R_{6a}S$ or $R_8R_{8a}R_7N$;

Y is $(CH_2)_n$, CH=CH, C(O), $NR_5$, O, $S(O)_p$ or

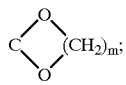

n is 0, 1 or 2;
m is 2 or 3;
p is 0, 1 or 2;
q is 0 or 1;
$R_5$ is hydrogen, $C_1$–$C_{12}$alkyl, phenyl-$C_1$–$C_6$alkyl or phenyl, where the radicals phenyl-$C_1$–$C_6$alkyl or phenyl are unsubstitued or are substituted 1–5 times by $C_1$–$C_6$alkyl, $C_1$–$C_{12}$alkoxy and/or halogen;
$R_6$ and $R_{6a}$ independently of one another are $C_1$–$C_{12}$alkyl, phenyl-$C_1$–$C_6$alkyl or phenyl, where the radicals phenyl-$C_1$–$C_6$alkyl or phenyl are unsubstituted or are substituted 1–5 times by $C_1$–$C_6$alkyl, $C_1$–$C_{12}$alkoxy and/or halogen;
$R_7$, $R_8$ and $R_{8a}$ independently of one another are $C_1$–$C_{12}$alkyl, $C_3$–$C_{12}$cycloalkyl, phenyl-$C_1$–$C_6$alkyl or phenyl where the radicals phenyl-$C_1$–$C_6$alkyl or phenyl are unsubstituted or are substituted 1–5 times by $C_1$–$C_6$alkyl, $C_1$–$C_{12}$alkoxy, $R_6OC(O)$, CN and/or halogen or $R_7$ and $R_8$ together with the N atom to which they are attached, form a 5- or 6-membered ring which may additionally contain O or S atoms;
$R_9$, $R_{10}$ and $R_{11}$ independently of one another are $C_1$–$C_{12}$alkyl, $C_3$–$C_{12}$cycloalkyl, phenyl-$C_1$–$C_6$alkyl or phenyl, where the radicals phenyl-$C_1$–$C_6$alkyl or phenyl are unsubstituted or are substituted 1–5 times by $C_1$–$C_6$alkyl, $C_1$–$C_{12}$alkoxy and/or halogen;
$R_{12}$ and $R_{13}$ independently of one another are $C_1$–$C_{12}$alkyl, $C_3$–$C_{12}$cycloalkyl, phenyl-$C_1$–$C_6$alkyl or phenyl where the radicals phenyl $C_1$–$C_6$alkyl or phenyl are unsubstituted or are substituted 1–5 times by $C_1$–$C_6$alkyl, $C_1$–$C_{12}$alkoxy and/or halogen, or $R_{12}$ and $R_{13}$, together with the B atom to which they are attached, form a 5- or 6-membered ring;
$R_{14}$, $R_{15}$ and $R_{16}$ independently of one another are $C_1$–$C_{12}$alkyl, $C_2$–$C_{12}$alkenyl, $C_3$–$C_{12}$cycloalkyl, where the radicals $C_1$–$C_{12}$alkyl, $C_2$–$C_{12}$alkenyl, $C_3$–$C_{12}$cycloalkyl are unsubstituted or are substituted by $R_6OCO$ or CN, or $R_{14}$, $R_1$ and $R_{16}$ are phenyl-$C_1$–$C_6$alkyl, which is unsubstituted or is substituted one to five times by $C_1$–$C_6$alkyl, $C_1$–$C_{12}$alkoxy or halogen, or are phenyl which is unsubstituted or is substituted one to five times by $C_1$–$C_6$alkyl, $C_1$–$C_{12}$-alkoxy or halogen; and
G is a radical which is able to form positive ions, with the proviso that, if $R_1$, $R_2$ and $R_3$ are 2,4,6-trimethylphenyl, $R_4$ is not $C_2$–$C_{20}$alkyl or $C_2$–$C_8$alkenyl In combination with coinitiators these compounds are highly reactive initiators for the photopolymerization of ethylenically unsaturated compounds.

In the compounds of the formula I, at least one of the radicals $R_1$ and $R_2$, provided that they are not $R_9,R_{10}R_{11}Si$ substituted $C_1$–$C_{20}$alkyl, are each a phenyl ring which is substituted ortho to the bond to the boron atom or is another aromatic hydrocarbon radical which is sterically hindered ortho to the boron atom. Ortho-substitution here is generally understood to mean a bond in the o position of the aryl ring with respect to the boron central atom, thus including, for example, a fused-on ring. In accordance with this definition, therefore, some polycyclic aromatic hydrocarbons, for example naphthyl, are also rings (ring systems) which are substituted ortho to the bond to the boron central atom.

Aromatic hydrocarbons as may be present in the novel compounds may, for example, contain one or more, especially 1 or 2, heteroatoms. Examples of suitable heteroatoms are N, O, P or S, preferably N or O. Examples of aromatic hydrocarbon radicals are phenyl, α- and β-naphthyl, stilbenyl, biphenyl, o-, m-, p-terphenyl, triphenylphenyl, binaphthyl, anthracyl, phenanthryl, pyrenyl, furan-2-yl or furan-3-yl, thiophen-2-yl or thiophen-3-yl, pyridin-2-yl, pyridin-3-yl or pyridin-4-yl quinolyl or isoquinolyl.

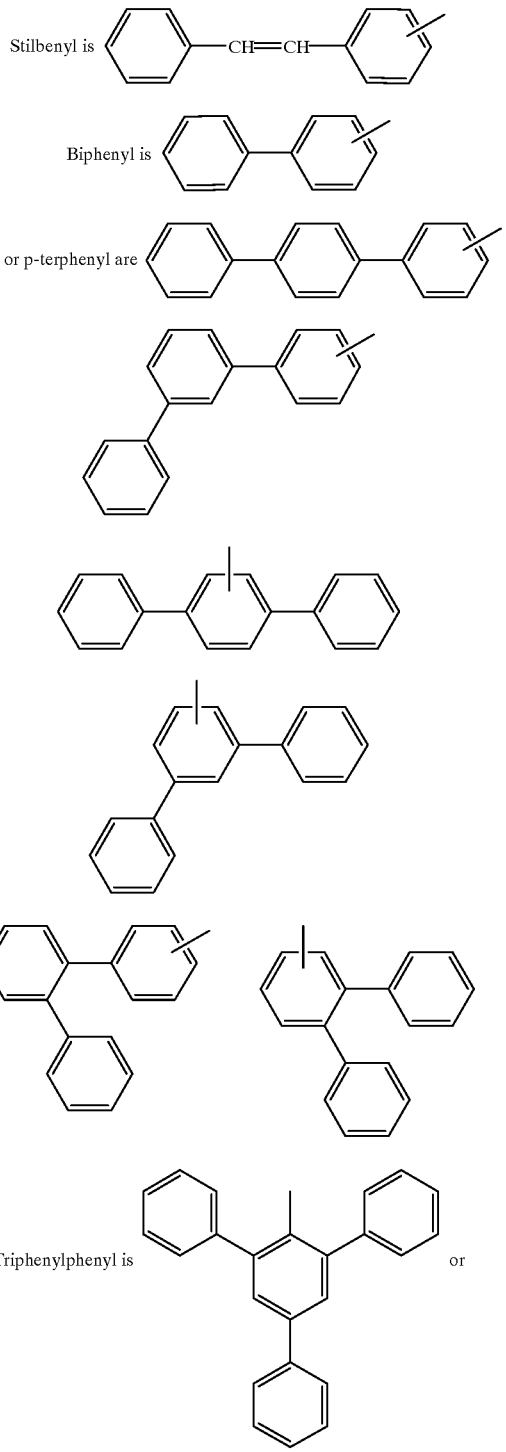

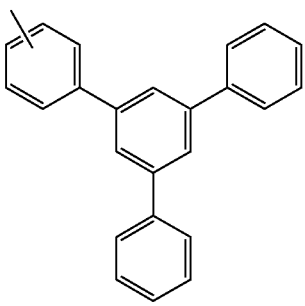

Binaphthyl is 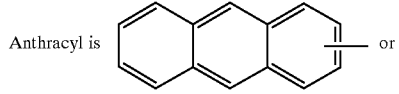

Anthracyl is 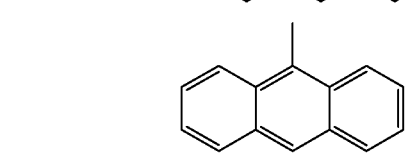 or

Phenanthryl is 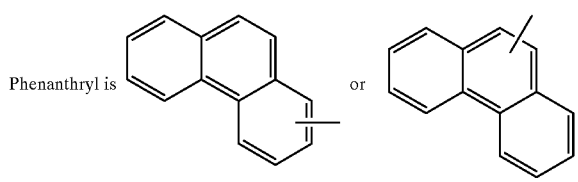 or

Pyrenyl is 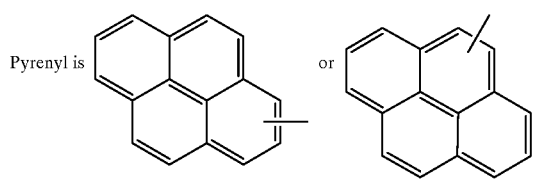 or

Furanyl is furan-2-yl or furan-3-yl. Thiophenyl is thiophen-2-yl or thiophen-3-yl. Pyridinyl is pyridin-2-yl, pyridin-3-yl or pyridin-4-yl. Quinolyl is

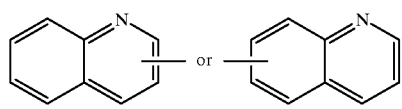 or

Isoquinolinyl is

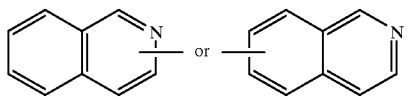 or

If the radicals phenyl, stilbenyl, biphenyl, o-, m- or p-terphenyl, triphenylphenyl, naphthyl, binaphthyl, anthracyl, phenanthryl, pyrenyl, ferrocenyl, furanyl, thiophenyl, pyridinyl, quinolinyl or isoquinolinyl are substituted, they are so one to four times, for example one, two or three times, especially one or two times. Substituents on the phenyl ring are preferably in positions 2, or in 2,6 or 2,4,6 on the phenyl ring.

$C_1$–$C_{20}$alkyl is linear or branched and is, for example, $C_1$–$C_{12}$, $C_1$–$C_8$, $C_1$–$C_6$ or $C_1$–$C_4$alkyl. Examples are methyl, ethyl, propyl, isopropyl, n-butyl, sec-butyl, isobutyl, tert-butyl, pentyl, hexyl, heptyl, 2,4,4-trimethylpentyl, 2-ethylhexyl, octyl, nonyl, decyl, undecyl, dodecyl, tetradecyl, pentadecyl, hexadecyl, heptadecyl, octadecyl, nonadecyl or eicosyl. For example, $R_4$ is $C_1$–$C_8$alkyl, in particular $C_1$–$C_6$alkyl, preferably $C_1$–$C_4$alkyl, for example methyl or butyl. Where $R_1$, $R_2$, $R_3$ and $R_4$ are $R_9R_{10}R_{11}$Si substituted $C_1$–$C_{20}$alkyl, then the alkyl radical is, for example, $C_1$–$C_{12}$alkyl, especially $C_1$–$C_8$alkyl, preferably $C_1$–$C_4$alkyl. Methyl is particularly preferred.

$C_1$–$C_{12}$alkyl and $C_1$–$C_6$alkyl are likewise linear or branched and have, for example, the definitions indicated above up to the corresponding number of C atoms. $R_5$, $R_6$, $R_7$, $R_8$, $R_9$, $R_{10}$, $R_{11}$, $R_{12}$ and $R_{13}$ are, for example, $C_1$–$C_8$alkyl, especially $C_1$–$C_6$alkyl, preferably $C_1$–$C_4$alkyl, for example methyl or butyl. $C_1$–$C_6$alkyl substituents for phenyl-$C_1$–$C_6$alkyl or phenyl are, in particular, $C_1$–$C_4$alkyl, for example methyl or butyl.

$C_2$–$C_{20}$alkyl which is interrupted one or more times by —O—, —S(O)$_p$— or —NR$_5$— is, for example, interrupted 1–9 times, for example 1–7 times or 1 or 2 times, by —O—, —S(O)$_p$— or —NR$_5$. This produces structural units such as, for example, —CH$_{2-O}$—CH$_3$, —CH$_2$CH$_2$—O—CH$_2$CH$_3$, —[CH$_2$CH$_2$O]$_y$—CH$_3$, where y=1–9, —(CH$_2$CH$_2$O)$_7$CH$_2$CH$_3$, —CH$_2$—CH(CH$_3$)-Q—CH$_2$—CH$_2$CH$_3$, —CH$_2$—CH(CH$_3$)—O—CH$_2$—CH$_3$, —CH$_2$SCH$_3$ or —CH$_2$—N(CH$_3$)$_2$.

$C_3$–$C_{12}$Cycloalkyl is, for example, cyclopropyl, cyclopentyl, cyclohexyl, cyclooctyl, cyclododecyl, especially cyclopentyl and cyclohexyl, preferably cyclohexyl.

$C_2$–$C_8$alkenyl radicals can be mono- or polyunsaturated and are, for example, allyl, methallyl, 1,1-dimethylallyl, 1-butenyl, 3-butenyl, 2-butenyl, 1,3-pentadienyl, 5-hexenyl or 7-octenyl, especially allyl. $R_4$ as $C_2$–$C_a$alkenyl is for example $C_2$–$C_6$alkenyl, especially $C_2$–$C_4$alkenyl.

Phenyl-$C_1$–$C_6$alkyl is, for example, benzyl, phenylethyl, α-methylbenzyl, phenylpentyl, phenylhexyl or α,α-dimethylbenzyl, especially benzyl. Preference is given to phenyl-$C_1$–$C_4$alkyl, especially phenyl-$C_1$–$C_2$alkyl. Substituted phenyl-$C_1$–$C_6$alkyl is substituted one to four times, for example once, twice or three times, especially once or twice, on the phenyl ring.

Phenyl-$C_1$–$C_6$alkylene has two free bonds of which one is on the phenylene ring and the other in the alkylene radical:

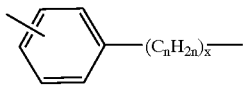

where x=1 to 6. Substitututed phenyl is substituted one to five times, for example once, twice or three times, especially once or twice, on the phenyl ring.

Naphthyl-$C_1$–$C_3$alkyl is for example, naphthylmethyl, naphthylethyl, naphthylpropyl or naphthyl-1-methylethyl, especially naphthylmethyl. The alkyl unit can be in either position 1 or position 2 of the naphthyl ring system. Substituted naphthyl-$C_1$–$C_3$alkyl is substituted one to four times, for example once, twice or three times, especially once or twice, on the aromatic rings.

$C_1$–$C_{12}$alkoxy denotes linear or branched radicals and is, for example, methoxy, ethoxy, propoxy, isopropoxy, n-butyloxy, sec-butyloxy, iso-butyloxy, tert-butyloxy, pentyloxy, hexyloxy, heptyloxy, 2,4,4-trimethylpentyloxy, 2-ethylhexyloxy, octyloxy, nonyloxy, decyl-oxy or dodecyloxy, especially methoxy, ethoxy, propoxy, isopropoxy, n-butyloxy, sec-butyloxy, iso-butyloxy, tert-butyloxy, preferably methoxy.

Halogen is fluorine, chlorine, bromine and iodine, especially fluorine, chlorine and bromine, preferably fluorine and chlorine.

Where $C_1$–$C_{20}$ alkyl is substituted one or more times by halogen, there are, for example, 1 to 3 or 1 or 2 halogen substituents on the alkyl radical.

Where $R_7$ and $R_8$, together with the N atom to which they are attached, form a 5- or 6-membered ring which may additionally contain O or S atoms, then the rings involved are, for example, saturated or unsaturated rings, for example aziridine, pyrrol, pyrrolidine, oxazole, thiazole, pyridine, 1,3-diazine, 1,2-diazine, piperidine or morpholine.

Radicals generally suitable as a counterion $G^+$ to the negative borate in the formula I are those which are able to form positive ions.

Examples of these are alkali metals, especially lithium or sodium, quaternary ammonium compounds, dye cations or cationic transition metal coordination complex compounds. Especially preferred are ammonium, tetraalkylammonium or dye cations. Examples of tetraalkylammonium are, in particular, tetramethylammonium or tetrabutylammonium, although trisalkylammonium ions, for example trimethylammonium, are also suitable. Suitable phosphonium and ammonium counterions are those of the formulae $^+PR_wR_xR_yR_z$ and $^+NR_wR_xR_yR_z$, where $R_w$, $R_x$, $R_y$, $R_z$ independently of one another are hydrogen, unsubstituted or substituted alkyl, cycloalkyl, alkenyl, phenyl or arylalkyl. Substituents for these alkyl, cycloalkyl, alkenyl, phenyl or arylalkyl radicals are, for example, halide, hydroxyl, heterocycloalkyl (e.g. epoxy, aziridyl, oxetanyl, furanyl, pyrrolidinyl, pyrrolyl, thiophenyl, tetrahydrofuranyl, etc.), dialkylamino, amino, carboxyl, alkyl- and arylcarbonyl and aryloxy- and alkoxycarbonyl.

The tetravalent nitrogen may also be part of a 5- or 6-membered ring, in which case this ring may in turn be fused to other ring systems. These systems may also contain additional heteroatoms, for example S, N, O.

The tetravalent nitrogen may also be part of a polycyclic ring system, for example azoniapropellane. These systems may also contain further heteroatoms, for example S, N, O.

Also suitable are polyammonium salts and polyphosphonium salts, especially the bis salts, in which it is possible for the same substituents to be present as described above for the "mono" compounds.

The ammonium salts and phosphonium salts may also be substituted by neutral dyes (e.g. thioxanthenenes, thioxanthones, coumarins, ketocoumarins, etc.). Such salts are obtained by the reaction of the ammonium salts and phosphonium salts, substituted by reactive groups (e.g. epoxy, amino, hydroxyl, etc.), with appropriate derivatives of neutral dyes. Corresponding examples are described in EP-A 224 967 (Quantacure QTX).

Similarly, ammonium salts and phosphonium salts can also be substituted by colourless electron acceptors (e.g. benzophenones); examples of these are Quantacure ABQ

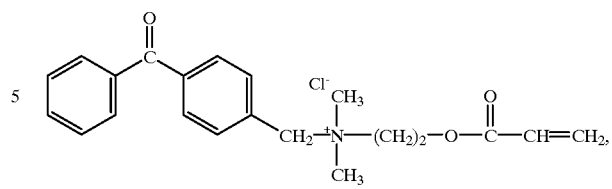

Quantacure BTC

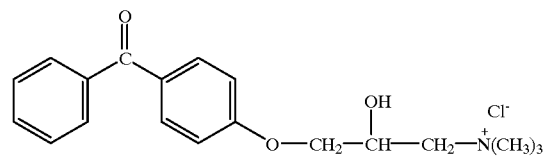

and Quantacure BTC

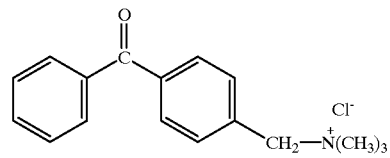

from International Bio-Synthetics.

Other quaternary ammonium compounds which are of interest are, for example, trimethylcetylammonium or cetylpyridinium compounds. Other examples to be used as positive counterions $G^+$ in the compound of the formual I include the following:

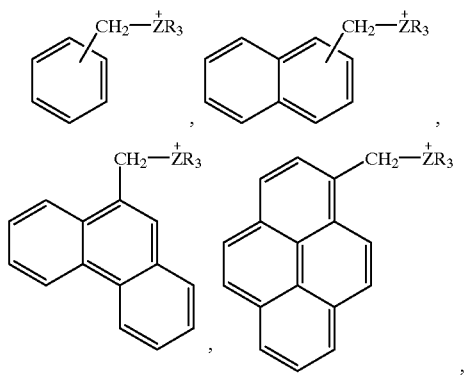

in which Z is P, N or S and R is an alkyl or aryl radical. Also suitable are compounds such as

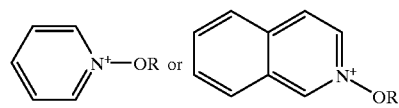

(described by Yagci et al. in J. Polym. Sci. Part A: Polymer Chem. 1992, 30, 1987 and Polymer 1993, 34(6), 1130) or compounds such as

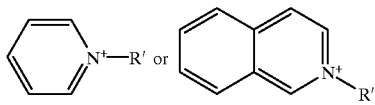

where R'=unsubstituted or substituted benzyl or phenacyl (described in JP-A Hei 7 70221). In these compounds, the aromatic rings in the pyridinium may also be substituted.

The term tetra ($C_1$–$C_4$alkyl)ammonium refers to compounds of the following formula: $N(C_1$–$C_4alkyl)^+_4$, where $C_1$–$C_4$alkyl can have the definitions given above up to the corresponding number of C atoms. Examples of appropriate ammonium compounds are tetramethylammonium, tetraethylammonium, tetrapropylammonium or tetrabutylammonium, especially tetramethylammonium and tetrabutylammonium. Benzyltri($C_1$–$C_4$alkyl)ammonium is $C_6H_5$—$CH_2$—$N(C_1$–$C_4alkyl)_3$+, where $C_1$–$C_4$alkyl can have the definitions given above up to the corresponding number of C atoms. Examples of such radicals are benzyltrimethylammonium, benzyltriethylammonium, benzyltripropylammonium and benzylbutylammonium, especially benzyltrimethylammonium and benzyltributylammonium.

Other positive counterions $G^+$ to the borate which can be employed are other onium ions, for example iodonium or sulfonium ions.

Examples of such counterions to the borate are radicals of the formula

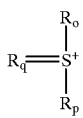

as described, for example, in EP-A 555 058 and EP-A 690 074. Also of interest as counterions are

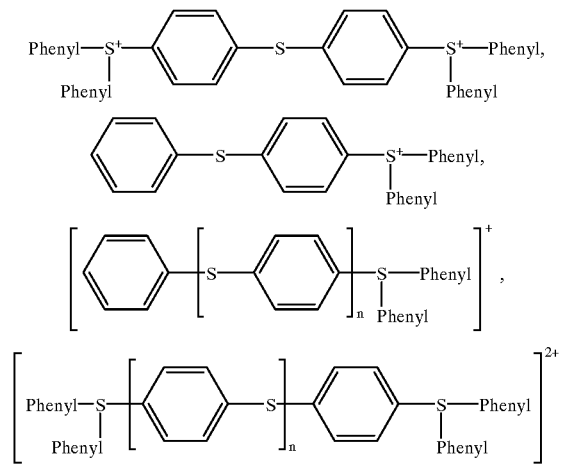

Further suitable counterions for the novel borates are cations of the formula

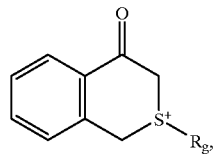

in which $R_g$ is an alkyl radical, especially ethyl, or benzyl, and where the aromatic ring can carry further substituents.

Other suitable counterions are halonium ions, especially diaryliodonium ions, as described for example in EP-A 334 056 and EP-A 562 897.

However, cations of ferrocenium salts are also suitable, as described, for example, in EP-A 94915 and EP-A 109 851, for example

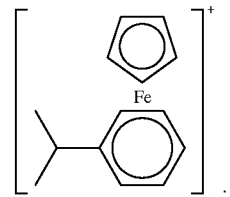

Other suitable "onium" cations, such as ammonium, phosphonium, sulfonium, iodonium, selonium, arsonium, tellonium and bismuthonium, are described, for example, in Japanese Patent Application Hei 6 266102.

Examples of cationic transition metal complex compounds which are suitable as counterions are described in U.S. Pat. No. 4,954,414. Of particular interest are bis(2,2'-bipyridine)(4,4'-dimethyl-2,2'-bipyridine)ruthenium, tris(4, 4'-dimethyl-2,2'-bipyridine)ruthenium, tris(4,4'-dimethyl-2, 2'-bipyridine)iron, tris(2,2',2"-terpyridine)ruthenium, tris(2, 2'-bipyridine)ruthenium and bis(2,2'-bipyridine)(5-chloro-1, 10-phenanthroline)ruthenium.

Dyes suitable as a counterion are those without acid groups, for example cations of triarylmethanes, for example malachite green, indolines, thiazines, for example methylene blue, xanthones, thioxanthones, oxazines, acridines, cyanines, rhodamines, phenazines, for example safranine, preferably cyanines, thioxanthones and safranine.

If the compounds of the formula I do not contain a dye as counterion and at the same time the corresponding borate is not sufficiently absorptive, then for the photopolymerization process it is expedient to add at least one coinitiator or electron aceptor compound, respectively. In this application the term coinitiator includes sensitizers and electron aceptor compounds, for example thioxanthones, reaction accelerators, for example amines, thiols, etc. Preferred are dyes. Examples of suitable dyes which can be added as coinitiators are described in U.S. Pat. No. 5,151,520. They are, for example, triarylmethanes, for example malachite green, indolines, thiazines, for example methylene blue, xanthones, thioxanthones, oxazine, acridine or phenazines, for example safranin. The above-described transition metal complex compounds or onion ion compounds can also be used as coinitiator.

Cationic, neutral or anionic dyes can be employed as coinitiators for the novel compounds. Particularly suitable cationic dyes are malachite green, methylene blue, safranin O, rhodamines of the formula III

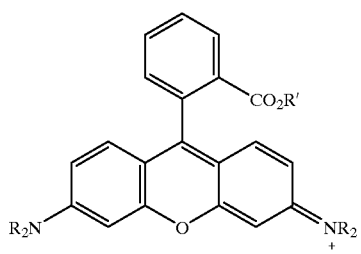

(III)

in which R and R' are alkyl radicals or aryl radicals, for example rhodamine B, rhodamine 6G or violamine R, and also sulforhodamine B or sulforhodamine G.

Other suitable dyes are fluorones, as described for example by Neckers et al. in J. Polym. Sci., Part A, Poly. Chem, 1995, 33, 1691–1703.

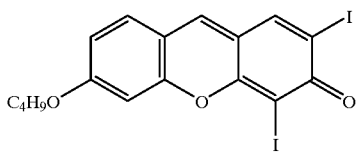

is particularly advantageous.

Examples of further suitable dyes are cyanines of the formula IV

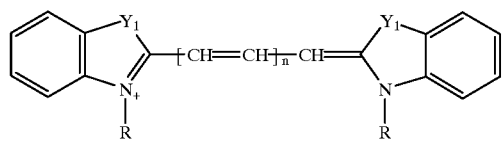

(IV)

in which R=alkyl; n=0,1,2,3 or 4 and $Y_1$=CH=CH, N—$CH_3$, $C(CH_3)_2$, O, S or Se. Preferred cyanines are those in which $Y_1$ in formula IV is $C(CH_3)_2$ or S.

The following dye compounds are also suitable as coinitiators:

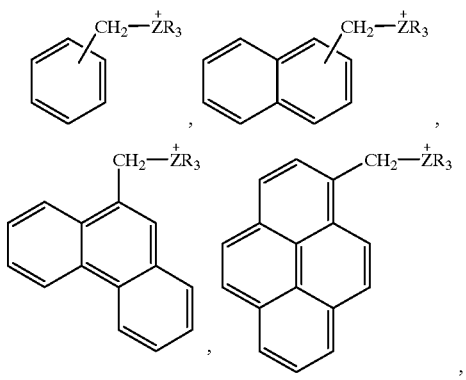

in which Z is P, N or S and R is an alkyl or aryl radical. Preferred compounds of the above formulae are those in which $ZR_3$ is $N(CH_3)_3$, $N(C_2H_5)_3$ or $P(C_6H_5)_3$.

Also suitable are compounds such as, for example,

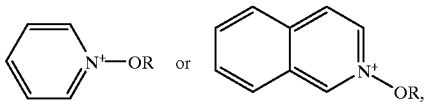

as described for example by Yagci et al. in J. Polym. Sci. Part A: Polymer Chem. 1992, 30,1987 and Polymer 1993, 34(6), 1130, or, for example,

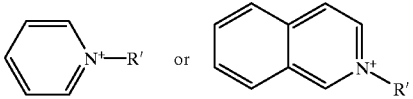

where R'=unsubstituted or substituted benzyl or phenacyl (described in JP-A Hei 7 70221). In these compounds, the aromatic pyridinium rings may also be substituted.

Other suitable dyes can be found, for example, in U.S. Pat. No. 4,902,604. These are azulene dyes. Of particular advantage as coinitiators for the novel compounds are the compounds 1–18 listed in columns 10 and 11 of this patent, in the Table. Examples of further suitable dyes are merocyanine dyes, as described in U.S. Pat. No. 4,950,581 from column 6, line 20 to column 9, line 57.

As coinitiators for the novel compounds and photoinitiators it is also possible to use coumarin compounds. Examples of these are given in U.S. Pat. No. 4,950,581 in column 11, line 20 to column 12, line 42.

Other suitable coinitiators are xanthones or thioxanthones as described, for example, in U.S. Pat. No. 4,950,581, column 12, line 44 to column 13, line 15.

Anionic dye compounds can also be employed as coinitiators. For instance, Rose Bengal, eosine or fluorescein are also suitable as coinitiators. Other suitable dyes, for example from the triarylmethane class or azo class, are described in U.S. Pat. No. 5,143,818.

Other suitable electron acceptor compounds are indicated later on below.

Preference is given to compounds of the formula I in which $R_1$ and $R_2$ independently of one another are phenyl which is substituted in at least one o-position by $C_1$–$C_6$alkyl, $OR_6$, $R_7R_8N$, $R_9R_{10}R_{11}Si$ and/or halogen, or $R_1$ and $R_2$ are o-terphenyl, naphthyl, binaphthyl, anthracyl, phenanthryl, pyrenyl, quinolinyl or isoquinolyl which radicals are unsubstituted or are substituted by $C_1$–$C_6$alkyl, $OR_6$, $R_7R_8N$, $R_9R_{10}R_{11}Si$ and/or halogen.

Further advantageous compounds of the formula I are those in which $R_3$ is phenyl, o-, m- or p-terphenyl, naphthyl, binaphthyl, anthracyl, phenanthryl, pyrenyl, quinolyl or isoquinolyl, which radicals are unsubstituted or substituted by $C_1$–$C_6$alkyl, $OR_6$, $R_7R_8N$, $R_9R_{10}R_{11}Si$ and/or halogen.

Compounds of the formula I deserving particular mention are those in which $R_4$ is phenyl, another aromatic hydrocarbon, $C_1$–$C_{12}$alkyl, $C_2$–$C_{12}$alkyl, which is interrupted by one or more O or $NR_5$ radicals, or is cyclopentyl, cyclohexyl, $C_2$–$C_{12}$alkenyl, benzyl or phenylethyl, which radicals are unsubstituted or are substituted by $OR_6$, $R_7R_8N$, $R_9R_{10}R_{11}Si$ and/or halogen.

Particular preference is given to those compounds of the formula I in which $R_1$, $R_2$ and $R_3$ independently of one another are $C_1$–$C_{20}$alkyl which is substituted by $R_9R_{10}R_{11}Si$.

Advantageous compounds of the formula I are those in which $R_4$ is $C_1$–$C_{20}$alkyl, substituted by $R_9R_{10}R_{11}Si$.

Preference is also given to the compounds of the formel I in which $R_1$ and $R_2$ are identical.

Preference is likewise given to compounds of the formula I in which $R_1$, $R_2$ and $R_3$ are identical.

Further preferred compounds of the formula I are those in which G is an alkali metal, a quaternary ammonium radical, a dye cation, a transition metal complex cation, a sulfonium, sulfoxonium, phosphonium or iodonium salt or a UV absorber containing a cationic group, or are a radical MgX or CaX, in which X is $C_1$–$C_8$alkoxy or halogen.

Other compounds of the formula I or I' which are of interest are those in which
$R_1$ and $R_2$ are $C_1$–$C_4$alkyl which are substituted by $R_9R_{10}R_{11}Si$ or are phenyl which is substituted 1–5 times by $C_1$–$C_4$alkyl, $OR_6$ and/or halogen; $R_{2a}$ is phenylene; $R_3$ is $C_1$–$C_4$alkyl which is substituted by $R_9R_{10}R_{11}Si$, or is phenyl which is unsubstituted or is substituted 1–5 times by $C_1$–$C_4$alkyl, $OR_6$, $R_7R_8N$ and/or halogen;
$R_4$ is unsubstituted or $R_9R_{10}R_{11}Si$ substituted $C_1$–$C_4$alkyl or unsubstituted or halogen-substituted phenyl;
m is 2 or 3; E is $R_8R_{8a}R_7N$; $R_6$ is $C_1$–$C_4$alkyl; $R_7$, $R_8$ and $R_{8a}$ independently of one another are $C_1$–$C_4$alkyl or benzyl; $R_9$, $R_{10}$ and $R_{11}$ are $C_1$–$C_4$alkyl and G is tetra($C_1$–$C_4$alkyl)ammonium or benzyl-tri($C_1$–$C_4$alkyl)ammonium.

The compounds of the formula I can be obtained, for example, by reacting triorganylboranes (A) with organometallic reagents, for example alkyllithium compounds or Grignard reagents:

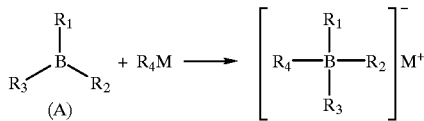

M is, for example, an alkali metal, such as Li or Na, or is MgX in which X is a halogen atom, especially Br.

Another possibility for preparing compounds of the formula I is, for example, the reaction of alkyldihaloboranes and alkyloxy- or aryloxydihaloboranes (B) with organometallic compounds, for example, Grignard reagents or lithium organyl compounds:

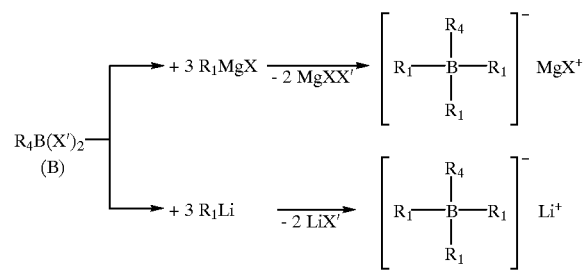

X is halogen, especially Br, and X' is halogen, alkoxy or aryloxy. The definitions of the other radicals are as indicated above.

Where G in the above formula I is a positive radical other than lithium or magnesium, these compounds can be obtained, for example, by means of cation exchange reactions.

The compounds of the formula I' are obtained, for example, by reacting triorganylboranes which are substituted by the group E as defined above to the borate in accordance with one of the methods set out above.

When working with organometallic reactions, the reaction conditions are generally familiar to the skilled worker. Thus the reaction is expediently carried out in an inert organic solvent, for example an ether or aliphatic hydrocarbon, for example diethyl ether, tetrahydrofuran or hexane.

Suitable organometallic reagents for preparing the novel polyborates are, for example, the lithium compounds of the corresponding aliphatic and aromatic hydrocarbons. The preparation of Grignard reagents is familiar to the skilled worker and is described in various textbooks and other publications.

The reaction with the organometallic reagent is expediently carried out with the exclusion of air in an inert gas atmosphere, for example under nitrogen. The reaction is generally performed with cooling to 0° C. or below followed by heating to room temperature.

It is expedient to stir the reaction mixture. The products are isolated and purified by methods likewise generally known to the skilled worker, for example chromatography, recrystallization, etc.

Where the novel compounds of the formula I contain a dye radical as cation, they are prepared by the cation exchange reaction of an appropriate borate salt with a dye. Examples of the borate salts suitable for the exchange are the lithium, magnesium, sodium, ammonium or tetraalkylammonium salts.

Where the novel compounds of the formula I contain a transition metal complex as cation, these compounds are prepared in analogy to the method described in U.S. Pat. No. 4,954,414, column 7, section 2.

Preparation of triorganylboranes (A): The preparation of some alkyldiarylboranes is described, for example, by A. Pelter et al. in Tetrahedron 1993, 49, 2965. The synthesis of some triarylboranes has been disclosed by Doty et al. in J. Organomet. Chem. 1972, 38, 229, by Brown et al. in J. Organomet. Chem. 1981, 209, 1, Brown et al. in J. Amer. Chem. Soc. 1957, 79, 2302, and by Wittig et al. in Chem. Ber. 1955, 88, 962.

Preparation of aryldihaloboranes (B): The route to some alkyldihaloboranes (B) has been depicted by Brown et al. in JACS 1977, 99, 7097. Mikailov et al. in Zh. Obshch. Khim. 1959, 29, 3405 and Tuchagues et al. in Bull. Chim. Soc. France, 1967, 11, 4160 also describe the preparation of such compounds. The preparation of phenyldifluoroborane has been set out by Nahm et al. in J. Organomet. Chem. 1972, 35,9.

Tris(trimethylsilylmethyl)boranes can be prepared, for example, by the method described by Seyferth et al. in J. Amer. Chem. Soc. 1959,81,1844.

The boranes required as starting materials for the novel compounds can be obtained, for example, in accordance with one of the published methods cited above.

In accordance with the invention the compounds of the formula I can be used as photoinitiators for the photopolymerization of ethylenically unsaturated compounds and mixtures comprising such compounds.

This can be carried out in combination with at least one coinitiator or electron acceptor respectively.

This use can also be implemented in combination with another photoinitiator and/or other additives.

The invention therefore also relates to photopolymerizable compositions comprising
(a) at least one ethylenically unsaturated photopolymerizable compound and (b) at least one compound of the formula Ia or Ia'

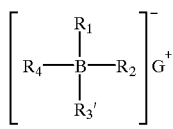

(Ia)

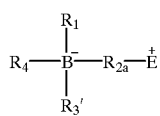

(Ia')

in which $R_1$, $R_2$, $R_{2}a$, $R_4$, E and G are as defined above and
$R_3'$ is $R_9R_{10}R_{11}Si$ substituted $C_1$–$C_{20}$alkyl, $C_1$–$C_4$alkyl, phenyl or another aromatic hydrocarbon, with or without any heteroatom, where the phenyl radical or the other aromatic hydrocarbon radicals are unsubstituted or are substituted 1–5 times by $C_1$–$C_{20}$alkyl, $C_2$–$C_{20}$alkyl which is interrupted by one or more radicals O, $S(O)_p$ or $NR_5$, or are substituted by $OR_6$, $R_6S(O)_p$, $R_6S(O)_2O$, $R_7R_8N$, $R_6OC(O)$, $R_7R_8NC(O)$, $R_9C(O)$, $R_9R_{10}R_{11}Si$, $R_9R_{10}R_{11}Sn$, $R_{12}R_{13}B$, halogen, $R_9R_{10}P(O)_q$ and/or CN, it being possible for the composition to comprise, in addition to components (a) and (b), other photoinitiators and/or other additives.

The unsaturated compounds may include one or more olefinic double bonds. They may be of low (monomeric) or high (oligomeric) molecular mass. Examples of monomers containing a double bond are alkyl or hydroxyalkyl acrylates or methacrylates, for example methyl, ethyl, butyl, 2-ethylhexyl or 2-hydroxyethyl acrylate, isobornyl acrylate, methyl methacrylate or ethyl methacrylate. Silicone acrylates are also advantageous. Other examples are acrylonitrile, acrylamide, methacrylamide, N-substituted (meth)acrylamides, vinyl esters such as vinyl acetate, vinyl ethers such as isobutyl vinyl ether, styrene, alkyl- and halostyrenes, N-vinylpyrrolidone, vinyl chloride or vinylidene chloride.

Examples of monomers containing two or more double bonds are the diacrylates of ethylene glycol, propylene glycol, neopentyl glycol, hexamethylene glycol or of bisphenol A, and 4,4'-bis(2-acryl-oyloxyethoxy)diphenylpropane, trimethylolpropane triacrylate, pentaerythritol triacrylate or tetraacrylate, vinyl acrylate, divinylbenzene, divinyl succinate, diallyl phthalate, triallyl phosphate, triallyl isocyanurate or tris(2-acryloylethyl) isocyanurate.

Examples of polyunsaturated compounds of relatively high molecular mass (oligomers) are acrylisized epoxy resins, acrylisized polyesters, polyesters containing vinyl ether or epoxy groups, and also polyurethanes and polyethers. Further examples of unsaturated oligomers are unsaturated polyester resins, which are usually prepared from maleic acid, phthalic acid and one or more diols and have molecular weights of from about 500 to 3000. In addition it is also possible to employ vinyl ether monomers and oligomers, and also maleate-terminated oligomers with polyester, polyurethane, polyether, polyvinyl ether and epoxy main chains. Of particular suitability are combinations of oligomers which carry vinyl ether groups and of polymers as described in WO 90/01512. However, copolymers of vinyl ether and maleic acid-functionalized monomers are also suitable. Unsaturated oligomers of this kind can also be referred to as prepolymers.

Particularly suitable examples are esters of ethylenically unsaturated carboxylic acids and polyols or polyepoxides, and polymers having ethylenically unsaturated groups in the chain or in side groups, for example unsaturated polyesters, polyamides and polyurethanes and copolymers thereof, alkyd resins, polybutadiene and butadiene copolymers, polyisoprene and isoprene copolymers, polymers and copolymers containing (meth)acrylic groups in side chains, and also mixtures of one or more such polymers.

Examples of unsaturated carboxylic acids are acrylic acid, methacrylic acid, crotonic acid, itaconic acid, cinnamic acid, and unsaturated fatty acids such as linolenic acid or oleic acid. Acrylic and methacrylic acid are preferred.

Suitable polyols are aromatic and, in particular, aliphatic and cycloaliphatic polyols. Examples of aromatic polyols are hydroquinone, 4,4'-dihydroxydiphenyl, 2,2-di(4-hydroxyphenyl)propane, and also novolaks and resols. Examples of polyepoxides are those based on the above-mentioned polyols, especially the aromatic polyols, and epichlorohydrin. Other suitable polyols are polymers and copolymers containing hydroxyl groups in the polymer chain or in side groups, examples being polyvinyl alcohol and copolymers thereof or polyhydroxyalkyl methacrylates or copolymers thereof. Further polyols which are suitable are oligoesters having hydroxyl end groups.

Examples of aliphatic and cycloaliphatic polyols are alkylenediols having preferably 2 to 12 C atoms, such as ethylene glycol, 1,2- or 1,3-propanediol, 1,2-, 1,3- or 1,4-butanediol, pentanediol, hexanediol, octanediol, dodecanediol, diethylene glycol, triethylene gicyol, polyethylene glycols having molecular weights of preferably from 200 to 1500, 1,3-cyclopentanediol, 1,2-, 1,3- or 1,4-cyclohexanediol, 1,4-dihydroxymethylcyclohexane, glycerol, tris(P-hydroxyethyl)amine, trimethylolethane, trimethylolpropane, pentaerythritol, dipentaerythritol and sorbitol.

The polyols may be partially or completely esterified with one carboxylic acid or with different unsaturated carboxylic acids, and in partial esters the free hydroxyl groups may be modified, for example etherified or esterified with other carboxylic acids.

Examples of esters are:
trimethylolpropane triacrylate, trimethylolethane triacrylate, trimethylolpropane trimethacrylate, trimethylolethane trimethacrylate, tetramethylene glycol dimethacrylate, triethylene glycol dimethacrylate, tetraethylene glycol diacrylate, pentaerythritol diacrylate, pentaerythritol triacrylate, pentaerythritol tetraacrylate, dipentaerythritol diacrylate, dipentaerythritol triacrylate, dipentaerythritol tetraacrylate, dipentaerythritol pentaacrylate, dipentaerythritol hexaacrylate, tripentaerythritol octaacrylate, pentaerythritol dimethacrylate, pentaerythritol trimethacrylate, dipentaerythritol dimethacrylate, dipentaerythritol tetramethacrylate, tripentaerythritol octamethacrylate, pentaerythritol diitaconate, dipentaerythritol trisitaconate, dipentaerythritol pentaitaconate, dipentaerythritol hexaitaconate, ethylene glycol diacrylate, 1,3-butanediol diacrylate, 1,3-butanediol dimethacrylate, 1,4-butanediol diitaconate, sorbitol triacrylate, sorbitol tetraacrylate, pentaerythritol-modified triacrylate, sorbitol tetra methacrylate, sorbitol pentaacrylate, sorbitol hexaacrylate, oligoester acrylates and methacrylates, glycerol diacrylate and triacrylate, 1,4-cyclohexane diacrylate, bisacrylates and bismethacrylates of polyethylene glycol with a molecular weight of from 200 to 1500, or mixtures thereof.

Also suitable as components (a) are the amides of identical or different, unsaturated carboxylic acids with aromatic, cycloaliphatic and aliphatic polyamines having preferably 2 to 6, especially 2 to 4, amino groups. Examples of such polyamines are ethylenediamine, 1,2- or 1,3-propylenediamine, 1,2-, 1,3- or 1,4-butylenediamine, 1,5-pentylenediamine, 1,6-hexylenediamine, octylenediamine, dodecylenediamine, 1,4-diaminocyclohexane, isophoronediamine, phenylenediamine, bisphenylenediamine, di-β-aminoethyl ether, diethylenetriamine, triethylenetetramine, di(β-aminoethoxy)- or di(β-aminopropoxy)ethane. Other suitable polyamines are polymers and copolymers, preferably with additional amino groups in the side chain, and oligoamides having amino end groups. Examples of such unsaturated amides are methylenebisacrylamide, 1,6-hexamethylenebisacrylamide, diethylenetriaminetrismethacrylamide, bis(methacrylamidopropoxy)ethane, β-methacrylamidoethyl methacrylate and N[(β-hydroxyethoxy)ethyl]acrylamide.

Suitable unsaturated polyesters and polyamides are derived, for example, from maleic acid and from diols or diamines. Some of the maleic acid can be replaced by other dicarboxylic acids. They can be used together with ethylenically unsaturated comonomers, for example styrene. The polyesters and polyamides may also be derived from dicarboxylic acids and from ethylenically unsaturated diols or diamines, especially from those with relatively long chains of, for example 6 to 20 C atoms. Examples of polyurethanes are those composed of saturated or unsaturated diisocyanates and of unsaturated or, respectively, saturated diols.

Polybutadiene and polyisoprene and copolymers thereof are known. Examples of suitable comonomers are oletins, such as ethylene, propene, butene and hexene, (meth)acrylates, acrylonitrile, styrene or vinyl chloride. Polymers with (meth)acrylate groups in the side chain are likewise known. They may, for example, be reaction products of epoxy resins based on novolaks with (meth)acrylic acid, or may be homo- or copolymers of vinyl alcohol or hydroxyalkyl derivatives thereof which are esterified with (meth)acrylic acid, or may be homo- and copolymers of (meth)acrylates which are esterified with hydroxyalkyl (meth)acrylates.

The photopolymerizable compounds can be used alone or in any desired mixtures. It is preferred to use mixtures of polyol (meth)acrylates.

Binders as well can be added to these novel compositions, and this is particularly expedient when the photopolymerizable compounds are liquid or viscous substances. The quantity of binder may, for example, be 5–95%, preferably 10–90% and especially 40–90%, by weight relative to the overall solids content. The choice of binder is made depending on the field of application and on properties required for this field, such as the capacity for development in aqueous and organic solvent systems, adhesion to substrates and sensitivity to oxygen.

Examples of suitable binders are polymers having a molecular weight of about 5000 to 2000000, preferably 10000 to1000000. Examples are: homo- and copolymers of acrylates and methacrylates, for example copolymers of methyl methacrylate/ethyl acrylate/methacrylic acid, poly(alkyl methacrylates), poly(alkyl acrylates); cellulose esters and cellulose ethers, such as cellulose acetate, cellulose acetobutyrate, methylcellulose, ethylcellulose; polyvinylbutyral, polyvinylformal, cyclized rubber, polyethers such as polyethylene oxide, polypropylene oxide and polytetrahydrofuran; polystyrene, polycarbonate, polyurethane, chlorinated polyolefins, polyvinyl chloride, vinyl chloride/vinylidene copolymers, copolymers of vinylidene chloride with acrylonitrile, methyl methacrylate and vinyl acetate, polyvinyl acetate, copoly(ethylene/vinyl acetate), polymers such as polycaprolactam and poly(hexamethylenadipamide), and polyesters such as poly(ethylene glycol terephtalate) and poly(hexamethylene glycol succinate).

The unsaturated compounds can also be used as a mixture with non-photopolymerizable, film-forming components. These may, for example, be physically drying polymers or solutions thereof in organic solvents, for instance-nitrocellulose or cellulose acetobutyrate. They may also, however, be chemically and/or thermally curable (heat-curable) resins, examples being polyisocyanates, polyepoxides and melamine resins. The use of heat-curable resins at the same time is important for use in systems known as hybrid systems, which in a first stage are photopolymerized and in a second stage are crosslinked by means of thermal aftertreatment.

The invention additionally provides compositions which in addition to components (a) and (b) comprise at least one coinitiator or electron acceptor, respectively (c), for example a neutral, cationic or anionic dye or a UV absorber.

Suitable dyes (c) are described above. Other suitable examples are benzoxanthene, benzothioxanthene, pyronine or porphyrin dyes. Particularly preferred are compositions containing cyanine derivatives as a dye. Particularly preferred are cyanines of the formula IV, where n is 1–4, Y is $C(CH_3)_2$ or S and R is $C_1$–Cloalkyl.

Examples of UV absorbers which are suitable as coinitiator or electron acceptor, respectively, (c) are thioxanthone derivatives, coumarins, benzophenone, benzophenone derivatives or derivatives of hexaarylbisimidazole. Examples of suitable hexaarylbisimidazole derivatives are described in U.S. Pat. Nos. 3,784,557, 4,252,887, 4,311,783, 4,459,349, 4,410,621 and 4,622,286. Of particular advantage are 2-o-chlorophenyl-substituted derivatives, such as 2,2'-bis(o-chlorophenyl)-4,4',5,5'-tetraphenyl-1,1'-bisimidazole. Other UV absorbers suitable in this context are, for example, polycyclic aromatic hydrocarbons, for example anthracene or pyrene, and the triazines described in EP-A-1 37 452, in DE-A-27 18 254 and in DE-A-22 43 621. Further suitable triazines can be found in U.S. Pat. No. 4,950,581, column 14, line 60 to column 18, line 44. Of particular advantage are trihalomethyltriazines, for example 2,4-bis(trichloromethyl)-6-(4-styrylphenyl)-s-triazine.

Other suitable coinitiators or electron acceptors (c) are benzoteridinediones (described in JP Hei 02 113002), substituted benzophenones (e.g. Michler's Ketone, Quantacure ABQ, Quantacure BPQ and Quantacure BTC from International Biosynthetics), trichloromethyltriazine (described in JP Hei 01 033548), metal complexes (described in JP Hei 04 261405), porphyrins (described in JP Hei 06 202548 and JP Hei 06 195014), coumarins and ketocoumarins (described in U.S. Pat. No. 4,950,581 and JP Hei 06 175557), p-aminophenyl compounds (described in EP-A 475153), xanthenes (described in JP Hei 06 175566) or pyrylium, thiopyrylium and selenopyrylium dyes (described in JP Hei 06 175563).

Also suitable as coinitiators and electron acceptors are readily reducible compounds. The term readily reducible compound refers in this context also to compounds described in U.S. Pat. No. 4,950,581, including for example iodonium salts, sulfonium salts, organic peroxides, compounds containing carbon halide bonds (trichloromethyltriazines, heterocyclic sulfur compounds and other photoinitiators (α-amino ketones). Examples of other additives are heterocycles as described in the patents and patent applications U.S. Pat. No. 5,168,032, JP 02 244050, JP 02 0542683, JP 01 017048 and DE 383308.

Examples of further additives are aromatic imines described in U.S. Pat. No. 5,079,126, and aromatic diazo compounds described in U.S. Pat. No. 5,200,292 (e.g. iminoquinone diazides), thiols, described in U.S. Pat. No. 4,937,159 and thiols and N,N-dialkylaniline described in U.S. Pat. No. 4,874,685. It is also possible to employ two or more of the abovementioned coinitiators or electron acceptors and additives in combination.

As already mentioned, it is advantageous to combine the novel borate compounds with coinitiators, inter alia sensitizers (that means energy transfer compounds). In this context, additionally and particularly, combinations with two or more different sensitizers, for example mixtures of the novel borate comopunds with "onium" salts and thioxanthones or coumarins or dyes, are highly effective. Preferred "onium" salts in these mixtures are diphenyliodonium hexafluorophosphate, (p-octyloxyphenyl)-(phenyl) iodonium hexafluorophosphate, or corresponding other anions of these compounds, for example the halides; but also sulfonium salts, for example triarylsulfonium salts (Cyracure™ UVI 6990, Cyracure™ UVI-6974 from Union Carbide; Degacure® KI 85 from Degussa or SP-150 und SP-170 from Asahi Denka). Preference is given, for example, to a mixture of the novel borate compounds with diphenyliodonium hexafluorophosphate and isopropylthioxanthone, to a mixture of the novel borate compounds with (p-octyloxyphenyl)(phenyl)iodonium hexafluorophosphate and isopropylthioxanthone, and to a mixture of the novel borate compounds with

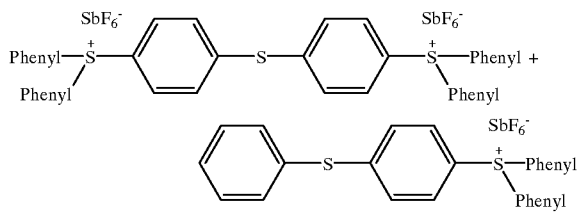

(=Cyracure® UVI-6974) and isopropylthioxanthone.

However, it is also particularly advantageous to add yet another photoinitiator, of the α-amino ketone type, to the abovementioned mixtures. For example, mixtures of the novel borates with onium salts and thioxanthones or dyes and α-amino ketones are highly effective. A preferred example is the mixture of the novel borate compounds with diphenyliodonium hexafluorophosphate or (p-octylphenyl) (phenyl)iodonium hexafluorophosphate, isopropylthioxanthone and (4-methylthiobenzoyl)methyl-1-morpholinoethane.

The invention also provides a composition comprising in addition to components (a) and (b) at least one neutral, anionic or cationic dye or a thioxanthone and an onium compound. The invention additionally provides a composition of this kind additionally comprising a free-radical photoinitiator, especially an α-amino ketone compound.

The invention provides, furthermore, a composition comprising in addition to components (a) and (b) at least one compound of the formula III

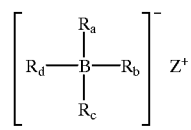

in which $R_a$, $R_b$, $R_c$ and $R_d$ independently of one another are $C_1$–$C_{12}$alkyl, trimethylsilylmethyl, phenyl, another aromatic hydrocarbon, $C_1$–$C_6$alkylphenyl, allyl, phenyl-$C_1$–$C_6$alkyl, $C_2$–$C_8$alkenyl, $C_2$–$C_8$alkynyl, $C_3$–$C_{12}$cycloalkyl or saturated or unsaturated heterocyclic radicals, wherein the radicals phenyl, another aromatic hydrocarbon, phenyl-$C_1$–$C_6$alkyl, or saturated or unsaturated heterocyclic radicals are unsubstituted or substituted by 1–5 times by $C_1$–$C_{20}$alkyl, $C_2$–$C_{20}$alkyl which is interrupted by one ore more radicals O, S(O)$_p$ or NR$_5$, or are substituted by OR$_6$, R$_6$S(O)$_p$, R$_6$S(O)$_2$O, R$_7$R$_8$N, R$_6$OC(O), R$_7$R$_8$NC(O), R$_9$C(O), R$_9$R$_{10}$R$_{11}$Si, R$_9$R$_{10}$R$_{11}$Sn, R$_{12}$R$_{13}$B, halogen, R$_9$R$_{10}$P(O)$_q$, and/or CN, p is 0, 1 or 2;

q is 0 or 1;

$R_5$ is hydrogen, $C_1$–$C_{12}$alkyl, phenyl-$C_1$–$C_6$alkyl or phenyl, where the radicals phenyl-$C_1$14 $C_6$alkyl or phenyl are unsubstitued or are substituted 1–5 times by $C_1$–$C_6$alkyl, $C_1$–$C_{12}$alkoxy and/or halogen;

$R_6$ is $C_1$–$C_{12}$alkyl, phenyl-$C_1$–$C_6$alkyl or phenyl, where the radicals phenyl-$C_1$–$C_6$alkyl or phenyl are unsubstituted or are substituted 1–5 times by $C_1$–$C_6$alkyl, $C_1$–$C_{12}$alkoxy and/or halogen;

$R_7$ and $R_8$ independently of one another are $C_1$–$C_{12}$alkyl, $C_3$–$C_{12}$cycloalkyl, phenyl-$C_1$–$C_6$alkyl or phenyl where the radicals phenyl-$C_1$–$C_6$alkyl or phenyl are unsubstituted or are substituted 1–5 times by $C_1$–$C_6$alkyl, $C_1$–$C_{12}$alkoxy, R$_6$OC(O), CN and/or halogen or $R_7$ and $R_8$ together with the N atom to which they are attached, form a 5- or 6-membered ring which may additionally contain O or S atoms;

$R_9$, $R_{10}$ and $R_{11}$, independently of one another are $C_1$–$C_{12}$alkyl, $C_3$–$C_{12}$cycloalkyl, phenyl-$C_1$–$C_6$alkyl or phenyl, where the radicals phenyl-$C_1$–$C_6$alkyl or phenyl are unsubstituted or are substituted 1–5-times by $C_1$–$C_6$alkyl, $C_1$–$C_{12}$alkoxy and/or halogen;

$R_{12}$ and $R_{13}$ independently of one another are $C_1$–$C_{12}$alkyl, $C_3$–$C_{12}$cycloalkyl, phenyl-$C_1$–$C_6$alkyl or phenyl where the radicals phenyl-$C_1$–$C_6$alkyl or phenyl are unsubstituted or are substituted 1–5 times by $C_1$–$C_6$alkyl, $C_1$–$C_{12}$alkoxy and/or halogen, or $R_{12}$ and $R_{13}$, together with the B atom to which they are attached, form a 5- or 6-membered ring; and Z is a radical which is able to form positive ions, especially alkali metals, ammonium or tetralkylammonium.

The definitions of the radicals $R_5$–$R_{13}$, $C_1$–$C_{12}$alkyl, trimethylsilylmethyl, phenyl, other aromatic hydrocarbons, $C_1$–$C_6$alkylphenyl, allyl, phenyl-$C_1$–$C_6$alkyl, $C_2$–$C_8$alkenyl, $C_2$–$C_8$alkynyl, $C_3$–$C_{12}$cycloalkyl, saturated or unsaturated heterocyclic radical, radical which is able to form positive ions, alkali metal, ammonium or tetraalkylammonium are as indicated above.

The invention also provides a composition comprising at least one borate of the formula I or I' and at least one dye which changes or loses its colour during or after the radiation, which dye may also, as cation, be part of the compound of the formula I or 1'. Examples of such dyes are cyanine dyes or pyrylium dyes.

In addition to the photoinitiator the photopolymerizable mixtures may include various additives. Examples of these are thermal inhibitors, which are intended to prevent premature polymerization, examples being hydroquinone, hydroquinine derivatives, p-methoxyphenol, β-naphthol or sterically hindered phenols, such as 2,6-di-tert-butyl-p-cresol. In order to increase the stability on storage in the dark it is possible, for example, to use copper compounds, such as copper naphthenate, stearate or octoate, phosphorus compounds, for example triphenylphosphine, tributylphosphine, triethyl phosphite, triphenyl phosphite or tribenzyl phosphite, quaternary ammonium compounds, for example tetramethylammonium chloride or trimethylbenzylammonium chloride, or hydroxylamine derivatives, for example N-diethylhydroxylamine. To exclude atmospheric oxygen during the polymerization it is possible to add paraffin or similar wax-like substances which, being of inadequate solubility in the polymer, migrate to the surface in the beginning of polymerization and form a transparent surface layer which prevents the ingress of air. It is also possible to apply an oxygen-impermeable layer. Light stabilizers which can be added in a small quantity are UV absorbers, for example those of the hydroxyphenylbenzotriazole, hydroxyphenyl-benzophenone, oxalamide or hydroxyphenyl-s-triazine type. These compounds can be used individually or in mixtures, with or without sterically hindered amines (HALS).

Examples of such UV absorbers and light stabilizers are 1. 2-(2'-hydroxyphenyl)benzotriazoles for example 2-(2'-hydroxy-5'-methylphenyl)benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chlorobenzotriazole, 2-(3'-tert-butyl-2'-hydroxy-5'-methylphenyl)-5-chlorobenzotriazole, 2-(3'-sec-butyl-5'-tert-butyl-2'-hydroxyphenyl)benzotrizole, 2-(2'-hydroxy-4'-octoxyphenyl)benzotriazole, 2-(3',5'-di-tert-amyl-2'-hydroxyphenyl)benzotriazole, 2-(3',5'-bis-(α, α-dimethylbenzyl)-2'-hydroxyphenyl)benzotriazole, mixture of 2-(3'-tert-butyl-2'-hydroxy-5'-(2-octyloxycarbonylethyl)phenyl)-5-chlorobenzotriazole, 2-(3'-tert-butyl-5'-[2-(2-ethyl-hexyloxy)carbonylethyl]-2'-hydroxyphenyl)-5-chlorobenzotriazole, 2-(3'-tert-butyl-2'-hydroxy-5'-(2-methoxycarbonylethyl)phenyl)-5-chlorobenzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl) benzotriazole, 2-(3'-tert-butyl-5'-[2-(2-ethylhexyloxy) carbonylethyl]-2'-hydroxyphenyl)benzotriazole, 2-(3'-dodecyl-2'-hydroxy-5'-methylphenyl)benzotriazole, and 2-(3'-tert-butyl-2'-hydroxy-5'-(2-isooctyloxycarbonylethyl) phenylbenzotriazole, 2,2'-methylenebis[4-(1,1,3,3-tetramethylbutyl)-6-benzotriazol-2-yl-phenol]; transesterification product of 2-[3'-tert-butyl-5'-(2-methoxycarbonylethyl)-2'-hydroxy-phenyl]-benzotriazole with polyethylene glycol 300; [R—CH$_2$CH$_2$—COO(CH$_2$)$_3$]$_2$- where R=3'-tert-butyl-4'-hydroxy-5'-2H-benzotriazol-2-yl-phenyl.

2. 2-Hydroxybenzophenones, for example the 4-hydroxy-, 4-methoxy-, 4-octoxy-, 4-decyloxy-, 4-dodecyloxy-, 4-benzyloxy-, 4,2',4'-trihydroxy- and 2'-hydroxy-4,4'-dimethoxy derivative.

3. Esters of substituted or unsubstituted benzoicacids, for example 4-tert-butylphenyl salicylate, phenyl salicylate, octylphenyl salicylate, dibenzoylresorcinol, bis(4-tert-butylbenzoyl)resorcinol, benzoylresorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl- 4-hydroxybenzoate, and 2-methyl-4,6-di-tert-butylphenyl 3,5-di-tert-butyl-4-hydroxybenzoate.

4. Acrylates, for example isooctyl or ethyl α-cyano-β,β-diphenyl acrylate, methyl α-carbomethoxycinnamate, butyl or methyl α-cyano-β-methyl-p-methoxycinnamate, methyl α-carboxymethoxy-p-methoxycinnamate and N-(β-carbomethoxy-β-cyanovinyl)-2-methylindoline.

5. Sterically hindered amines, for example bis-(2,2,6,6-tetramethylpiperidyl) sebacate, bis-(2,2,6,6-tetramethylpiperidyi) succinate, bis-(1,2,2,6,6-pentamethylpiperidyl) sebacate, bis(1,2,2,6,6-pentamethylpiperidyl) n-butyl-3,5-di-tert-butyl-4-hydroxybenzylmalonate, condensation product of 1-hydroxyethyl-2,2,6,6-tetramethyl-4-hydroxypiperidine and succinic acid, condensation product of N,N'-bis-(2,2,6, 6-tetramethyl-4-piperidyl)hexa-methylenediamine and 4-tert-octylamino-2,6-dichloro-1,3,5-s-triazine, tris-(2,2,6, 6-tetramethyl-4-piperidyl) nitrilotriacetate, tetrakis-(2,2,6,6-tetramethyl-4-piperidyl)-1,2,3,4-butane tetraoate, 1,1'-(1,2-ethandiyl)bis(3,3,5,5-tetramethyl-piperazinone), 4-benzoyl-2,2,6,6-tetramethylpiperidine, 4-stearyloxy-2,2,6,6-tetramethylpiperidine, bis-(1,2,2,6,6-pentamethylpiperidyl) 2-n-butyl-2-(2-hydroxy-3,5-di-tert-butylbenzyl) malonate, 3-n-octyl-7,7,9,9-tetramethyl-1,3,8-triazaspiro-(4.5]decane-2,4-dione, bis-(1-octyloxy-2,2,6,6-tetramethylpiperidyl) sebacate, bis-(1-octyloxy-2,2,6,6-tetramethylpiperidyl) succinate, condensation product of N,N'-bis-(2,2,6,6-tetramethyl-4-piperidyl)hexamethylenediamine and 4-morpholino-2,6-dichloro-1,3,5-triazine, condensation product of 2-chloro-4,6-di-(4-n-butylamino-2,2,6,6-tetramethylpiperidyl)-1,3,5-triazine and 1,2-bis-(3-aminopropyl-amino)ethane, condensation product of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidine-2, 5-dione and 3-dodecyl-1-(1,2,2,6,6-penta-methyl-4-piperidyl)-pyrrolidine-2,5-dione.

6. Oxalamides, for example 4,4'-dioctyloxyoxanilide, 2,2'-diethoxyoxanilide, 2,2'-dioctyloxy-5,5'-di-tert-butyloxanilide, 2,2'-didodecyloxy-5,5'di-tert-butyloxanilide, 2-ethoxy-2'-ethyl-oxanilide, N,N'-bis-(3-dimethylaminopropyl)oxalamide, 2-ethoxy-5-tert-butyl-2'-ethyloxanilide and its mixture with 2-ethoxy-2'-ethyl-5,4'-di-tert-butyloxanilide, mixtures of o- and p-methoxy- and of o- and p-ethoxy-disubstituted oxanalides.

7. 2-(2-Hydroxyphenyl)-1,3,5-triazines, for example 2,4, 6-tris(2-hydroxy-4-octyloxyphenyl)-1,3,5-triazine, 2-(2-hydroxy-4-octyloxyphenyl)-4,6-bis-(2,4-dimethylphenyl)-1,3,5-triazine, 2 -(2,4-dihydroxyphenyl)-4,6-bis(2,4-dimethylphenyl)-1,3,5-triazine, 2,4-bis(2-hydroxy-4-propyloxy-phenyl)-6-(2,4-dimethylphenyt)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis (2,4-dimethylphenyl)-1,3,5-triazine, 2-[2-hydroxy-4-(2-hydroxy-3-butyloxy-propyloxy)phenyl]-4,6-bis(2,4-dimethylphenyl)-1,3,5-triazine, 2-[2-hydroxy-4-(2-hydroxy-3-octyloxy-propyloxy)phenyl]-4,6-bis(2,4-dimethylphenyl)-1,3,5-triazine, 2-[4-dodecyl/tridecyl-oxy-(2-hydroxypropyl)oxy-2-hydroxy-phenyl]-4,6-bis(2,4-dimethylphenyl)-1,3,5-triazine.

8. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythrityl diphosphite, tris-(2,4-di-tert-butylphenyl) phosphite, diisodecyl pentaerythrityl diphosphite, bis-(2,4-di-tert-butylphenyl) pentaerythrityl diphosphite, bis-(2,6-di-tert-butyl-4-methylphenyl) pentaerythrityl diphosphite, bis-isodecyloxy pentaerythrityl diphosphite, bis-(2,4-di-tert-butyl-6-methylphenyl) pentaerythrityl diphosphite, bis-(2,4,6-tri-tert-butylphenyl) pentaerythrityl diphosphite, tristearyl sorbityl triphosphite, tetrakis-(2,4-di-tert-butylphenyl)-4,4'-biphenylene diphosphonite, 6-isooctyloxy-2,4,8,10-tetra-tert-butyl-12H-dibenzo[d,g]-1,3,2-dioxaphosphocine, 6-fluoro-2,4,8,10-tetra-tert-butyl-12-methyl-dibenzo[d,g]-1,3,2-dioxaphosphocine, bis-(2,4-di-tert-butyl-6-methylphenyl) methyl phosphite and bis(2,4-di-tert-butyl-6-methylphenyl) ethyl phosphite.

To accelerate the photopolymerization it is possible to add amines, for example triethanolamine, N-methyidiethanolamine, p-dimethylaminobenzoate or Michler's ketone. The action of the amines can be intensified by the addition of aromatic ketones of the benzophenone type. Examples of amines which can be used as oxygen scavengers are substituted N,N-dialkylanilines, as are described in EP-A-339 841. Other accelerators, coinitiators and autoxidizers are thiols, thioethers, disulfides, phosphonium salts, phosphine oxides or phosphines, as described, for example, in EP-A-438 123, in GB-A-2 180 358 and in JP-A Hei 6 268309.

Photopolymerization can also be accelerated by adding further photosentisizers which shift or broaden the spectral sensitivity. These are, in particular, aromatic carbonyl compounds, for example benzophenone, thioxanthone, anthraquinone and 3-acylcoumarin derivatives, and also 3-(aroylmethylene)thiazolines, but also eosine, rhodamine and erythrosine dyes.

The curing process can be assisted by, in particular, compositions which are pigmented (for example with titanium dioxide), and also by adding a component which under thermal conditions forms free radicals, for example an azo compound such as 2,2'-azobis(4-methoxy-2,4-dimethylvaleronitrile), a triazene, diazo sulfide, pentazadiene or a peroxy compound, for instance a hydroperoxide or peroxycarbonate, for example t-butyl hydroperoxide, as described for example in EP-A-245 639.

Further customary additives, depending on the intended use, are fluorescent whiteners, fillers, pigments, dyes, wetting agents or levelling assistants. In order to cure thick and pigmented coatings it is appropriate to add glass microspheres or pulverized glass fibres, as described for example in U.S. Pat. No. 5,013,768.

The invention also provides compositions comprising as component (a) at least one ethylenically unsaturated photopolymerizable compound which is emulsified or dissolved in water.

Many variants of such radiation-curable aqueous prepolymer dispersions are commercially available. A prepolymer dispersion is understood as being a dispersion of water and at least one prepolymer dispersed therein. The concentration of water in these systems is, for example, from 5 to 80% by weight, in particular from 30 to 60% by weight. The concentration of the radiation-curable prepolymer or prepolymer mixture is, for example, from 95 to 20% by weight, in particular from 70 to 40% by weight. In these compositions the sum of the percentages given for water and prepolymer is in each case 100, with auxiliaries and additives being added in varying quantities depending on the intended use.

The radiation-curable, film-forming prepolymers which are dispersed in water and are often also dissolved are aqueous prepolymer dispersions of mono- or polyfunctional, ethylenically unsaturated prepolymers which are known per se, can be initiated by free radicals and have for example a content of from 0.01 to 1.0 mol of polymerizable double bonds per 100 g of prepolymer and an average molecular weight of, for example, at least 400, in particular from 500 to 10 000. Prepolymers with higher molecular weights, however, may also be considered depending on the intended application. Use is made, for example, of polyesters containing polymerizable C—C double bonds and having an acid number of not more than 10, of polyethers containing polymerizable C—C double bonds, of hydroxyl-containing reaction products of a polyepoxide, containing at least two epoxide groups per molecule, with at least one α,β-ethylenically unsaturated carboxylic acid, of polyurethane (meth)acrylates and of acrylic copolymers which contain α,β-ethylenically unsaturated acrylic radicals, as are described in EP-A-12 339. Mixtures of these prepolymers can likewise be used. Also suitable are the polymerizable prepolymers described in EP-A-33 896, which are thioether adducts of polymerizable prepolymers having an average molecular weight of at least 600, a carboxyl group content of from 0.2 to 15% and a content of from 0.01 to 0.8 mol of polymerizable C—C double bonds per 100 g of prepolymer. Other suitable aqueous dispersions, based on specific alkyl (meth)acrylate polymers, are described in EP-A-41 125, and suitable water-dispersible, radiation-curable prepolymers of urethane acrylates can be found in DE-A-29 36 039.

Further additives which may be included in these radiation-curable aqueous prepolymer dispersions are dispersion auxiliaries, emulsifiers, antioxidants, light stabilizers, dyes, pigments, fillers, for example talc, gypsum, silicic acid, rutile, carbon black, zinc oxide, iron oxides, reaction accelerators, levelling agents, lubricants, wetting agents, thickeners, flatting agents, antifoams and other auxiliaries customary in paint technology. Suitable dispersion auxiliaries are water-soluble organic compounds which are of high molecular mass and contain polar groups, examples being polyvinyl alcohols, polyvinylpyrrolidone or cellulose ethers. Emulsifiers which can be used are nonionic emulsifiers and, if desired, ionic emulsifiers as well.

In certain cases it may be of advantage to use mixures of two or more of the novel photoinitiators. It is of course also possible to use mixtures with known photoinitiators, for example mixtures with benzophenone, acetophenone derivatives, for example α-hydroxycycloalkyl phenyl ketones, dialkoxyacetophenones, α-hydroxy- or α-aminoacetophenones, 4-aroyl-1,3-dioxolanes, benzoin alkyl ethers and benzil ketals, monoacyl phosphine oxides, bisacylphosphine oxides, titanocenes, ferrocenes, anthraquinone, thioxanthones or xanthones.

Examples of particularly suitable photoinitiators are: 1-(4-dodecylbenzoyl)-1-hydroxy-1-methylethane, 1-(4-isopropylbenzoyl)-1-hydroxy-1-methylethane, 1-benzoyl-1-hydroxy-1-methylethane, 1-[4(2-hydroxyethoxy)-benzoyll-1-hydroxy-1-methylethane, 1-[4(acryloyloxyethoxy) benzoyl]-1-hydroxy-1-methylethane, diphenyl ketone, penyl-1-hydroxy-cyclohexyl ketone, (4-morpholinobenzoyl)-1-benzyl-1-dimethylaminopropane, 1-(3,4-di-methoxyphenyl)-2-benzyl-2-dimethylamino-butan-1-one, (4-methylthiobenzoyl)-1-methyl-1-morpholinoethane, benzil dimethyl ketal, bis (cyclopentadienyl)-bis(2,6-difluoro-3-pyrryl-phenyl) titanium, cyclopentadienyl-arene-iron(II) complex salts, for example ($\eta^6$-iso-propylbenzene)($\eta^5$-cyclopentadienyl)iron (II) hexafluorophosphate, trimethylbenzoyidiphenylphosphine oxide, bis(2,6-dimethoxy-benzoyl)-(2,4,4- trimethylpentyl)phosphine oxide, bis(2,4,6-trimethylbenzoyl)-2,4-dipentoxyphenylphosphine oxide or bis(2,4,6-trimethylbenzoyl)-phenylphosphine oxide. Other suitable additional photoinitiators can be found in U.S. Pat. No. 4,950,581 column 20, line 35 to column 21, line 35. Where the novel photoinitiators are employed in hybrid systems, use is made, in addition to the novel free-radical hardeners, of cationic photoinitiators, for example peroxide compounds, such as benzoyl peroxide (other suitable peroxides are described in U.S. Pat. No. 4,950,581 column 19, lines 17–25), aromatic sulfonium or iodonium salts as described for example in U.S. Pat. No. 4,950,581, column 18, line 60 to column 19, line 10 or cyclopentadienyl-arene-iron(II) complex salts, for example ($\eta^6$-Iso-propylbenzol) ($\eta^5$-cyclopentadien-yl)iron(II) hexafluorophosphate.

The invention therefore further provides compositions which in addition to the photoinitiator (b) also comprise at least one further photoinitiator (d) and/or other additives and/or coinitiators.

The photopolymerizable compositions include the photoinitiator (b) or the photoinitiators (b) and (d) expediently in a quantity of from 0.05 to 15% by weight, preferably from 0.1 to 5% by weight, based on the composition.
(The quantity indicated relates to the overall quantity of photoinitiator in the composition.)

Compositions comprising as photoinitiator (d) a titanocene, a ferrocene, a benzophenone, a benzoin alkyl ether, a benzil ketal, a 4-aroyl-1,3-dioxolane, a dialkoxyacetophenone, an α-hydroxy- or α-aminoacetophenone, an α-hydroxycycloalkyl phenyl ketone, a xanthone, a thioxanthone, an anthraquinone or a mono- or bisacylphosphine oxide, or mixtures thereof, as additional photoinitiator are of particular preference.

The photopolymerizable compositions can be used for various purposes, for example as printing ink, as a clear finish, as a white finish, for example for wood or metal, as a coating material, inter alia for paper, wood, metal or plastic, as a daylight-curable coating for the marking of buildings and roadmarking, for photographic reproduction techniques, for holographic recording materials, for image recording techniques or to produce printing plates which can be developed with organic solvents or with aqueous alkalis, for producing masks for screen printing, as dental filling compositions, as adhesives, as pressure-sensitive adhesives, as laminating resins, as etch resists or permanent resists, and as solder masks for electronic circuits, for producing three-dimensional articles by mass curing (UV curing in transparent moulds) or by the stereolithography technique, as is described, for example, in U.S. Pat. No. 4,575,330, to produce composite materials (for example styrenic polyesters, which may, if desired, contain glass fibres and other auxiliaries) and other thick-layered compositions, for coating or sealing electronic components, or as coatings for optical fibres.

The novel compounds may additionally be employed as initiators for emulsion polymerizations, as polymerization initiators for fixing ordered states of liquid-crystalline monomers and oligomers, or as initiators for fixing dyes on organic materials.

In coating materials, use is frequently made of mixtures of a prepolymer with polyunsaturated monomers, which may additionally include a monounsaturated monomer as well. It is the prepolymer here which primarily dictates the properties of the coating film, and by varying it the skilled worker is able to influence the properties of the cured film. The polyunsaturated monomer functions as a crosslinking agent which renders the film insoluble. The monounsaturated monomer functions as a reactive diluent, which is used to reduce the viscosity without the need to employ a solvent.

Unsaturated polyester resins are usually used in two-component systems together with a monounsaturated monomer, preferably with styrene. For photoresists, specific one-component systems are often used, for example polymaleimides, polychalcones or polyimides, as described in DE-A-23 08 830.

The novel compounds and mixtures thereof can also be used as free-radical photoinitiators or photoinitiating systems for radiation-curable powder coatings. The powder coatings can be based on solid resins and monomers containing reactive double bonds, for example maleates, vinyl ethers, acrylates, acrylamides and mixtures thereof. A free-radically UV-curable powder coating can be formulated by mixing unsaturated polyester resins with solid acrylamides (for example methyl methylacrylamidoglycolate) and a novel free-radical photoinitiator, such formulations being as described, for example, in the paper "Radiation Curing of Powder Coating", Conference Proceedings, Radtech Europe 1993 by M. Wittig and Th. Gohmann. The powder coatings can also contain binders, as are described, for example, in DE-A-42 28 514 and in EP-A-636 669. Free-radically UV-curable powder coatings can also be formulated by mixing unsaturated polyester resins with solid acrylates, methacrylates or vinyl ethers and with a novel photoinitiator (or photoinitiator mixture). The powder coatings may also comprise binders as are described, for example, in DE-A-42 28 514 and in EP-A-636 669. The UV-curable powder coatings may additionally comprise white or coloured pigments. For example, preferably rutiletitanium dioxide can be employed in concentrations of up to 50% by weight in order to give a cured powder coating of good hiding power. The procedure normally comprises electrostatic or tribostatic spraying of the powder onto the substrate, for example metal or wood, melting of the powder by heating, and, after a smooth film has formed, radiation-curing of the coating with ultraviolet and/or visible light, using for example medium-pressure mercury lamps, metal halide lamps or xenon lamps. A particular advantage of the radiation-curable powder coatings over their heat-curable counterparts is that the flow time after melting the powder particles can be delayed in order to ensure the formation of a smooth, high-gloss coating. In contrast to heat-curable systems, radiation-curable powder coatings can be formulated to melt at lower temperatures without the unwanted effect of shortening their lifetime. For this reason, they are also suitable as coatings for heat-sensitive substrates, for example wood or plastics. In addition to the novel photoinitiators, the powder coating formulations may also include UV absorbers. Appropriate examples are listed above in sections 1.–8.

The novel photocurable compositions are suitable, for example, as coating materials for substrates of all kinds, for example wood, textiles, paper, ceramics, glass, plastics such as polyesters, polyethylene terephthalate, polyolefins or cellulose acetate, especially in the form of films, and also metals such as Al, Cu, Ni, Fe, Zn, Mg or Co and GaAs, Si or $SiO_2$ to which it is intended to apply a protective layer or, by means of imagewise exposure, to generate an image.

Coating of the substrates can be carried out by applying to the substrate a liquid composition, a solution or a suspension. The choice of solvents and the concentration depend principally on the type of composition and on the coating technique. The solvent should be inert, i.e. it should not undergo a chemical reaction with the components and should be able to be removed again, after coating, in the course of drying. Examples of suitable solvents are ketones, ethers and esters, such as methyl ethyl ketone, isobutyl methyl ketone, cyclopentanone, cyclohexanone, N-methylpyrrolidone, dioxane, tetrahydrofuran, 2-methoxyethanol, 2-ethoxyethanol, 1-methoxy-2-propanol, 1,2-dimethoxyethane, ethyl acetate, n-butyl acetate and ethyl 3-ethoxypropionate. The solution is applied uniformly to a substrate by means of known coating techniques, for example by spin coating, dip coating, knife coating, curtain coating, brushing, spraying, especially by electrostatic spraying, and reverse-roll coating, and also by means of electrophoretic deposition. It is also possible to apply the photosensitive layer to a temporary, flexible support and then to coat the final substrate, for example a copper-clad circuit board, by transferring the layer via lamination.

The quantity applied (coat thickness) and the nature of the substrate (layer support) are dependent on the desired field of application. The range of coat thicknesses generally comprises values from about 0.1 $\mu$m to more than 100 $\mu$m.

The novel radiation-sensitive compositions find application as negative resists, having a very high sensitivity to light and being able to be developed in an aqueous alkaline medium without swelling. They are suitable as photoresists for electronics (electroplating resist, etch resist, solder resist), the production of printing plates, such as offset printing plates or screen printing plates, for use in chemical milling or as a microresist in the production of integrated circuits. The possible layer supports, and the processing conditions of the coating substrates, are just as varied.

The compounds according to the invention also find application for the production of one- or more-layered materials for the image recording ore image reproduction (copies, reprography), which may be uni- or polychromatic. Furthermore the materials are suitable for colour proofing systems. In this technology formulations containing microcapsules can be applied and for the image production the radiation curing can be followed by a thermal treatment. Such systems and technologies and their applications are for example disclosed in U.S. Pat. No. 5,376,459.

Substrates used for photographic information recordings include, for example, films of polyester, cellulose acetate or polymer-coated papers; substrates for offset printing formes are specially treated aluminium, substrates for producing printed circuits are copper-clad laminates, and substrates for producing integrated circuits are silicon wafers. The layer thicknesses for photographic materials and offset printing formes is generally from about 0.5 $\mu$m to 10 $\mu$m, while for printed circuits it is from 1.0 $\mu$m to about 100 $\mu$m.

Following the coating of the substrates, the solvent is removed, generally by drying, to leave a coat of the photoresist on the substrate.

The term "imagewise" exposure includes both exposure through a photomask comprising a predetermined pattern, for example a slide, exposure by means of a laser beam, which for example is moved under computer control over the surface of the coated substrate and in this way produces an image, and irradiation with computer-controlled electron beams.

Following the imagewise exposure of the material and prior to development, it may be advantageous to carry out thermal treatment for a short time. In this case only the exposed sections are thermally cured. The temperatures employed are generally 50–150° C., preferably 80–130° C.; the period of thermal treatment is in general between 0.25 and 10 minutes.

The photocurable composition may additionally be used in a process for producing printing plates or photoresists as is described, for example, in DE-A-40 13 358. In such a process the composition is exposed for a short time to visible light with a wavelength of at least 400 nm, without a mask, prior to, simultaneously with or following imagewise irradiation.

After the exposure and, if implemented, thermal treatment, the unexposed areas of the photosensitive coating are removed with a developer in a manner known per se.

As already mentioned, the novel compositions can be developed by aqueous alkalis. Particularly suitable aqueous-alkaline developer solutions are aqueous solutions of tetraalkylammonium hydroxides or of alkali metal silicates, phosphates, hydroxides and carbonates. Minor quantities of wetting agents and/or organic solvents may also be added, if desired, to these solutions. Examples of typical organic solvents, which may be added to the developer liquids in small quantities, are cyclohexanone, 2-ethoxyethanol, toluene, acetone and mixtures of such solvents.

Photocuring is of great importance for printings, since the drying time of the binder is a critical factor for the production rate of graphic products, and should be in the order of fractions of seconds. UV-curable inks are particularly important for screen printing.

As already mentioned above, the novel mixtures are highly suitable also for producing printing plates. This application uses, for example, mixtures of soluble linear polyamides or styrene/butadiene and/or styrene/isoprene rubber, polyacrylates or polymethyl methacrylates containing carboxyl groups, polyvinyl alcohols or urethane acrylates with photopolymerizable monomers, for example acrylamides and/or methacrylamides, or acrylates and/or methacrylates, and a photoinitiator. Films and plates of these systems (wet or dry) are exposed over the negative (or positive) of the printed original, and the uncured parts are subsequently washed out using an appropriate solvent.

Another field where photocuring is employed is the coating of metals, in the case, for example, of the coating of metal plates and tubes, cans or bottle caps, and the photocuring of polymer coatings, for example of floor or wall coverings based on PVC.

Examples of the photocuring of paper coatings are the colourless varnishing of labels, record sleeves and book covers.

Also of interest is the use of the novel compounds for curing shaped articles made from composite compositions. The composite compound consists of a self-supporting matrix material, for example a glass fibre fabric, or alternatively, for example, plant fibres [cf. K. -P. Mieck, T. Reussmann in Kunststoffe 85 (1995), 366–370], which is impregnated with the photocuring formulation. Shaped parts comprising composite compounds, when produced using the novel compounds, attain a high level of mechanical stability and resistance. The novel compounds can also be employed as photocuring agents in moulding, impregnating and coating compositions as are described, for example, in EP-A-7086. Examples of such compositions are gel coat resins, which are subject to stringent requirements regarding curing activity and yellowing resistance, and fibre-reinforced mouldings, for example, light diffusing panels which are planar or have lengthwise or crosswise corrugation. Techniques for producing such mouldings, such as hand lay-up, spray lay-up, centrifugal casting or filament winding, are described, for example, by P. H. Selden in "Glasfaserverstarkte Kunststoffe", page 610, Springer Verlag Berlin-Heidelberg-New York 1967. Examples of articles which can be produced by these techniques are boats, fibre board or chipboard panels with a double-sided coating of glass fibre-reinforced plastic, pipes, containers, etc. Further examples of moulding, impregnating and coating compositions are UP resin gel coats for mouldings containing glass fibres (GRP), such as corrugated sheets and paper laminates. Paper laminates may be based on urea resins or melamine resins. Prior to production of the laminate, the gel coat is produced on a support (for example a film). The novel photocurable compositions can also be used for casting resins or for embedding articles, for example electronic components, etc. Curing is carried out using medium-pressure mercury lamps as are conventional in UV curing. However, there is also particular interest in less intense lamps, for example of the type TL 40W/03 or TL40W/05. The intensity of these lamps corresponds approximately to that of sunlight. It is also possible to use direct sunlight for curing. A further advantage is that the composite composition can be removed from the light source in a partly cured, plastic state and can be shaped, with full curing taking place subsequently.

The compositions and compounds according to the invention can be used for the production of waveguides, optical switches wherein advantage is taken of the development of a difference in the index of refraction between irradiated and unirradiated areas.

The use of photocurable compositions for imaging techniques and for the optical production of information carriers is also important. In such applications, as already described above, the layer (wet or dry) applied to the support is irradiated through a photomask with UV or visible light, and the unexposed areas of the layer are removed by treatment with a solvent (=developer). Application of the photocurable layer to metal can also be carried out by electrodeposition. The exposed areas are polymeric through crosslinking and are therefore insoluble and remain on the support. Appropriate colouration produces visible images. Where the support is a metallized layer, the metal can, following exposure and development, be etched away at the unexposed areas or reinforced by electroplating. In this way it is possible to produce electronic circuits and photoresists.

The photosensitivity of the novel compositions extends in general from about 200 nm through the UV region into the infrared region (about 20000 μm, in particular 1200 nm) and therefore spans a very broad range. Suitable radiation is present, for example, in sunlight or light from artificial light sources. Consequently, a large number of very different types of light sources are employed. Both point sources and arrays ("lamp carpets") are suitable. Examples are carbon arc lamps, xenon arc lamps, medium-, high- and low-pressure mercury lamps, possibly with metal halide dopes (metal-halogen lamps), microwave-stimulated metal vapour lamps, excimer lamps, superactinic fluorescent tubes, fluorescent lamps, argon incandescent lamps, electronic flashlights, photographic flood lamps, electron beams and X-rays, produced by means of synchrotrons or laser plasma. The distance between the lamp and the substrate to be exposed in accordance with the invention may vary depending on the intended application and the type and output of lamp, and may be, for example, from 2 cm to 150 cm. Laser light sources, for example excimer lasers, such as krypton F lasers for exposure at 248 nm. are especially suitable. Lasers in the visible region and in the IR region can also be employed. In this case, the high sensitivity of the novel materials is very advantageous. By this method it is possible to produce printed circuits in the electronics industry, lithographic offset printing plates or relief printing plates, and also photographic image recording materials.

The invention therefore also provides a process for the photopolymerization of nonvolatile monomeric, oligomeric or polymeric compounds containing at least one ethylenically unsaturated double bond, which comprises adding to the abovementioned compounds at least one compound of the formula I according to claim 1 in which G is a dye radical, or at least one compound of the formula I or I' according to claim 1 in combination with an electron acceptor and irradiating the mixture with light from the infrared region through the UV region to a wavelength of 200 nm.

The invention additionally provides for the use of the above-described composition for preparing pigmented and unpigmented coatings, printing inks, powder coatings, printing plates, adhesives, dental compositions, waveguides, optical switches, colour proofing systems, glass fibre cable coatings, screen printing stencils, resist materials, materials for encapsulating electrical and electronic components, for photographical reproductions, for producing composites, for producing magnetic recording materials, for producing three-dimensional objects by stereolithography and as image recording material, especially for holographic recordings.

The invention additionally provides a coated substrate which is coated on at least one surface with a composition as described above, and describes a process for the photographic production of relief images, in which a coated substrate is subjected to imagewise exposure and then the unexposed portions are removed with a solvent. Of particular advantage in this context is the laser beam exposure already mentioned above.

The novel compounds of the formulae I and I' are white powders which are stable in air. As already mentioned above, in the compounds at least two aryl radicals are substituted in at least one o-position of the aryl ring. These compounds surprisingly reveal an extremely good reactivity as free-radical photoinitiators.

Those compounds of the formulae I and I' which contain electron-attracting groups are in general also acid-stable and can be employed in acidic polymerizable formulations as photo hardeners.

The borate compounds according to the invention can be used not only as initiators for photopolymerization reactions but also as thermal polymerization initiators.

Subsequently, the invention also provides for the use of the compounds of formula I or I', or Ia or Ia', as initiators for the thermal polymerization of compounds containing ethylenically unsaturated double bonds, and a process for the thermal polymerization of compounds containing ethylenically unsaturated double bonds, which comprises employing at least one compound of the formula I or 1', or 1a or 1a' as polymerization initiator.

The examples which follow illustrate the invention in more detail. Parts and percentages are, as in the remainder of the description and in the claims, by weight, unless stated otherwise.

Where alkyl radicals having more than three carbon atoms are referred to without any mention of specific isomers, the n-isomers are meant in each case.

I. Preparation of the boranes

Compound 1: Dimesitylphenylborane 1.1 equivalents of 1.6 M butyllithium in hexane (37.5 ml, 0.066 mol) are added over the course of 15 minutes at −78° C. to a solution of 9.42 g (0.06 mol) of bromobenzene in 80 ml of tetrahydrofuran (TH F). The reaction mixture is stirred at this temperature for 3 h. Then 16.1 g (0.06 mol) of solid dimesityifluoroborane are added, and the mixture is allowed to warm to room temperature and stirred for a further hour. The mixture is poured into 500 ml of water and the resulting suspension is filtered. The product is purified by trituration with boiling methanol, to give 16.9 g (86% of theory) of the product as a white solid with a melting range of 185–187° C. The shifts δ in the ¹H NMR, measured in CDCl₃ are 7.50 ppm (d,2,J=7 Hz), 7.46 ppm (t, 1,J=10 Hz), 7.50 ppm (br t, 2, J=7 Hz), 6.82 ppm (s,4), 2.30 ppm (s,6) and 2.00 ppm (s,12).

Compound 2: Phenylbis(bromomesityl)borane 1.1 equivalents of 1.6 M butyllithium in hexane (6.25 ml, 0.011 mol) are added over the course of 15 minutes at −78° C. to a suspension of 2.78 g (0.01 mol) of dibromomesitylene in 20 ml of (THF). The reaction mixture is stirred at this temperature for one hour, and then 0.63 g (0.58 ml, 0.005 mol) of phenyldifluoroborane is added over the course of 10 minutes. The mixture is then allowed to warm to room temperature, and is stirred for 2 hours and then poured into water. Following extraction with 100 ml of ethyl acetate, the organic phase is dried over magnesium sulfate and, following filtration, is concentrated, giving 2.59 g of a white solid. Recrystallization from hexane gives 1.27 g (i.e. 52% of theory) of the borane in pure form, with a melting point of 215–218° C. The shifts δ in the ¹H NMR measured in CDCl₃ are 7.49 ppm (t,1,J=7 Hz), 7.46 ppm (d, 2, J=7 Hz), 7.35 ppm (t,2,J=7 Hz), 6.91 ppm (s,2), 2.42 ppm (s,6), 2.13 ppm (s,6) and 1.98 ppm (s,6).

Compound 3–10, 14, 15:

Compound 3 is prepared by the method described for compound 2 using the appropriate starting materials. Compounds 4–10, 14 and 15 are each obtained in analogy to compound 1 using the appropriate starting materials. The compounds and their structures are set out in Table 1.

Compound 12: m-Chlorophenyldimesitylborane

The preparation of compound 12 is described in J. Organomet. Chem. 1981, 209,1. It has a melting point of 151° C. In the ¹H NMR (300 MHz, CDCl₃) it shows the following shifts δ [ppm] and coupling constants J [Hz]: 7.46 (s,1), 7.43 (d,1,J=9), 7.36 (d,1,J=7), 7.27 (t,1,J=7.5), 6.82 (s,4), 2.30 (s,6), 1.98 (s,12).

Compound 13: p-Bromophenyldimesitylborane

The preparation of Compound 13 is described in J. Organomet. Chem. 1972, 38, 229. It has a melting point of 184–185° C. In ¹H NMR (300 MHz, CDCl₃) it shows the following shift δ [ppm] and coupling constants J [Hz]: 7.48 (d,2,J=8), 7.36 (d,2,J=8), 6.81 (s,4), 2.30 (s,6), 1.99 (s,12).

TABLE 1

$$R_3 \overset{R_1}{\underset{}{\overset{|}{B}}} R_2$$

| Compound | $R_1$ | $R_2$ | $R_3$ | Melting point [° C.] | ¹H NMR 300 MHz; CDCl₃ δ [ppm]; J [Hz] |
|---|---|---|---|---|---|
| 3 | Dichloro-mesityl | Dichloro-mesityl | Phenyl | 212–216 | 7.52 (t, 1, J=7) 7.43–7.33 (m, 4) 2.58 (s, 6) 2.10 (s, 12) |
| 4 | Chloro-mesityl | Chloro-mesityl | Phenyl | 182–187 | 7.49 (t, 1, J=7) 7.46 (d, 2, J=7) 7.35 (t, 2, J=7) 6.91 (s, 2) 2.39 (s, 6) 2.08 (s, 6) 1.99 (s, 6) |
| 5 | Mesityl | Mesityl | p-Fluorophenyl | 119–120 | 7.52 (dd, 2, J=8, 5 5, 5) 7.2 (t, 2, J=8, 5) 6.81 (s, 4) 2.30 (s, 6) 1.99 (s, 12) |
| 6 | Mesityl | Mesityl | m-Fluorophenyl | 185–186 | 7.32–7.28 ((m, 2) 7.17–7.11 (m, 2) 6.82 (s, 4) 2.30 (s, 6) 1.99 (s, 12) |
| 7 | Mesityl | Mesityl | 3,4-Difluoro-phenyl | 207–208 | 7.31–7.23 (m, 2) 7.16–7.07 (m, 1) 6.82 (s, 4) 2.30 (s, 6) 1.99 (s, 12) |
| 8 | Mesityl | Mesityl | 3,5-Difluoro-phenyl | 199–200 | 6.97 (br d, 2, J=8) 6.92–6.82 (m, 1) 6.82 (s, 4) 2.30 (s, 6) 1.98 (s, 12) |
| 9 | Mesityl | Mesityl | 3,5-Bis(trifluoromethyl)phenyl | 139–140 | 7.97 (s, 1) 7.92 (s, 2) 6.85 (s, 4) 2.32 (s, 6) 1.95 (s, 12) |
| 10 | Mesityl | Mesityl | 3-Bromo-5-fluoro-phenyl | 145–148 | 7.40 (s, 1) 7.33 (dt, 1, J=8, 2) 7.09 (dd, 1, J=4, 2) 6.82 (s, 4) 2.30 (s, 6) 1.98 (s, 12) |
| 11 | Mesityl | Mesityl | p-Chlorophenyl | 180–181 | 7.44 (d, 2, J=8) 7.31 (d, 2, J=8) 6.82 (s, 4) 2.30 (s, 6) 1.99 (s, 12) |
| 14 | Chloro-mesityl | Chloro-mesityl | p-Bromophenyl | 160–172 | 7.50 (d, 2, J=8) 7.32 (d, 2, J=8) 6.91 (s, 2) 2.39 (s, 6) 2.07 (s, 6) 1.98 (s, 6) |
| 15 | Mesityl | Mesityl | 4-Bromo-2,5-dimethyl-phenyl | 204–205 | 7.31 (s, 1) 7.04 (s, 1) 6.76 (s, 4) 2.28 (s, 6) 2.27 (s, 3) 1.99 (s, 3) 1.95 (s, 12) |

Compound 16: Trimesitylborane

The preparation of compound 16 is described in J. Am. Chem. Soc. 1957, 79, 2302. It has a melting point of 197–198° C. In ¹H NMR (300 MHz, CDCl₃) it shows the following shift δ [ppm] and coupling constants J [Hz]: 6.72 (s,6), 2.25 (s,9), 1.97 (s,18).

Compound 17: Butylbis(chlorodutyl)borane

A mixture of 1.21 g (0.05 mol) of magnesium, 11.50 g (0.05 mol) of dichlorodurene and one crystal of iodine in 40 ml THF is refluxed for 22 hours. The resulting Grignard solution is cooled to 0° C., and 3.55 g (3.14 ml, 0.025 mol) of boron trifluoride ethyl etherate are added dropwise over the course of 15 minutes. The reaction mixture is allowed to warm to room temperature and is then refluxed for one hour. After cooling to 0° C., a solution of 1.6 M butyllithium in hexane (15.6 ml, 0.025 mol) is added, and the reaction mixture is allowed to warm to room temperature and is stirred for 2 hours. The mixture is then poured into water and subjected to extraction with 200 ml of ethyl acetate. The organic phase is dried over magnesium sulfate, filtered and concentrated, giving 12.6 g of a white solid. Chromatography (SiO₂/hexane) gives 5.19 g (i.e. 51% of theory) of the pure borane, with a melting point of 145–147° C. The shifts δ in the ¹H NMR, measured in CDCl₃ are at 2.32 ppm (s,12), 2.20 ppm (s,12), 1.83 ppm (br t,2,J=6.5 Hz), 1.36–1.25 ppm (m,4), 0.83 ppm (t,3,J=7 Hz).

Compound 18: Tris(o-tolyl)borane

The preparation of compound 18 is described in Chem. Ber. 1955, 88, 962. It has a melting point of 67–69° C. In the ¹H NMR (300 MHz, CDCl₃) it shows the following shifts δ [ppm] and coupling constants J [Hz]: 7.35–7.29 (m,3), 7.17–7.07 (m,9), 2.07 (s,9).

Compound 20: Butyidimesitylborane

Compound 20 is prepared similarly to compound 17 using the appropriate starting materials. The compound is an oil, which in the ¹H NMR (300 MHz, CDCl₃) shows the following shifts δ [ppm] and coupling constants J [Hz]: 6.77 (s,4), 2.26 (s,6), 2.20 (S,12), 1.88 (t,2,J=7), 1.52–1.16 (m,4), 0.85 (t,3,J=7).

Compound 21: Methyldimesitylborane

Compound 21 is prepared similarly to compound 17 using the appropriate starting materials. The compound has a melting point of 78–79° C., and in the ¹H NMR (300 MHz, CDCl₃) shows the following shifts δ [ppm] and coupling constants J [Hz]: 6.73 (s,4), 2.23 (s,6), 2.20 (s,12), 1.46 (s,3).

Compound 22: Dimesitylphenylborane

Compound 22 corresponds to the compound from Example 1.

Compound 23: Tris(trimethylsilylmethyl)borane

The preparation of compound 23 is described in J. Am. Chem. Soc., 1959, 81, 1844. It is an oil, which in the ¹H NMR (300 MHz, CDCl₃) shows the following shifts δ [ppm] and coupling constants J [Hz]: 0.67 (s,6), —0.23 (s,27).

Compound 24: Tris(chilormesityl)borane

Compound 24 is prepared similarly to compound 1 using the appropriate starting materials. The compound has a melting point of 188–189° C., and in the ¹H NMR (300 MHz, CDCl₃) shows the following shifts δ (ppm) and coupling constants J [Hz]: 6.84 (s,1.5), 6.82 (s,1.5), 2.35 (s,9), 2.16–1.85 (m,18).

Compound 25: Tris(dichlormesityl)borane

Gaseous chlorine is passed for 45 minutes at ciC into a suspension of 0,01 g of FeCl₃ and 0.74 g of trimesitylborane in 10 ml of carbon tetrachloride. After warming to room temperature, the reaction mixture is washed with thiosulfate solution, dried over sodium sulfate and concentrated. Chromatography (SiO₂/Hexane) of the residue gives 0.20 g (i.e. 17% of theory) of the title compound, with a melting point of over 230° C. In the ¹H NMR (300 MHz, CDCl₃) the compound shows the following shifts δ [ppm] and coupling constants J (Hz) auf: 2.55 (s,9), 2.08 (s,18).

Compound 26: Tri(m-tolyl)borane

The compound is prepared by the method described in Chem. Ber. 1955,88,962.

Compound 27: Tri(p-tolyl)borane

The compound is prepared by the method described in Chem. Ber. 1955,88,962.

Compound 28: o-Tolyl-dimesitylborane

The compound is prepared by the method described in Example 1 using the appropriate precursors. The melting point is 128–129° C., and the signals in the ¹H NMR spectrum (recorded in CDCl₃) are at 7.22 ppm (dt,1,J=7 Hz), 7.14–7.01 ppm (m,3), 6.70 ppm (s,4), 2.25 ppm (s,6), 2.01 ppm (-,3) and 1.90 ppm (s,12).

Compound 29: (p-Dimethylaminophenyl)dimesitylborane

The compound is prepared by the method described in Example 1 using the appropriate precursors. The melting point is 164–165° C., and the signals in the ¹H NMR spectrum (recorded in CDCl₃) are at 7.37 ppm (d,2,J=9 Hz), 6.73 ppm (s,4), 6.52 ppm (d,2,J=9 Hz), 2.96 ppm (s,6), 2.23 ppm (s,6) and 1.99 ppm (s,12).

Compound 33: Bis(dichloromesityl)(4'-brombiphenyl)borane

General procedure for preparing aryldimesitylboranes 1.1 equivalents of butyllithium (0.077 mol) in hexane are added over the course of 15 minutes at −78° C. to a solution of 0.07 mol of 4,4'-dibromobiphenyl in 100 ml of tetrahydrofuran (THF). The reaction mixture is stirred at the temperature for 3 h. Then 0.07 mol of solid bis(dichloromesityl)fluoroborane are added, and the mixture is allowed to warm to room temperature and is stirred for one hour more. The mixture is poured into 500 ml of water and subjected to extraction with ethyl acetate. Drying over MgSO₄, filtration and concentration give a pale yellow solid. The product is purified with boiling acetonitrile. The shifts δ in the ¹H NMR are 7.60–7.47 ppm (m,8); 2.59 ppm (s,6); 2.13 ppm (s,12).

Compound 35: Dimesityl-1-naphthylborane

This compound is prepared by a method similar to that described for compound 33. The melting point is 170–171° C. and the shifts δ in the ¹H NMR are at 7.98 ppm (d, 1, J=8 Hz); 7.89 ppm (d, 2, J=9 Hz); 7.56 ppm (dd, 1, J=7 Hz); 7.51–7.44 ppm (m, 2); 7.33–7.27 ppm (m, 1); 6.85 ppm (s, 4); 2.36 ppm (s, 6); 2.00 ppm (br s, 12).

II. Preparation of the borates

General method of preparing borates from triorganylboranes

EXAMPLE 1a

Tetramethylammonium methyl-dimesityl-phenylborate 1.1 equivalents of methyllithium (0.0101 mol) in ether are added at 0° C. to a suspension of 3.0 g (0.0092 mol) of dimesitylphenylborane in 20 ml of diethyl ether at a rate such that the temperature does not exceed 5° C. The reaction mixture is allowed to warm to room temperature and is stirred for 2 h. The resulting 2-phase mixture is poured into a vigorously stirred solution of 1.2 g (0.011 mol) of tetramethylammonium chloride in 50 ml of water. The precipitated solid is filtered off, washed with hexane and water and dried in vacuo, giving 3.6 g (95% of theory) of the product as a white solid with a melting point of 249–250° C. In the ¹¹B NMR (CD₃OCD₃) the shift signal δ appears at −8,71 ppm.

Further examples:

The compounds of Examples 2a–18a, 20a–23a, 1b, 3b–6b, 9b, 11b, 12b, 17b, 22b 23b–e, 24a–b, 25a–29a, 32a, 33a, 34a and 35a–f are prepared similarly to the compound from Example 1a using the appropriate borane compounds (2–29). The structures and physical data of the compounds are given in Table 2.

General method of preparing borates from alkyldihaloboranes

EXAMPLE 18b

Tetramethylammonium butyl-tris(o-methylphenyl)borate

A small portion of solution of 5.13 g (0.03 mol) 2-bromotoluene in 30 ml of THF is added to a suspension of 0.73 g (0.03 mol) of magnesium turnings in 10 ml of THF. The reaction mixture is heated until the Grignard reaction begins. When the reaction begins, heating is discontinued and the remainder of the 2-bromotoluene solution is added dropwise at a rate such that a slight reflux is retained. Following the addition, heating is recommenced until the remainder of the magnesium has been consumed. In a different reaction vessel, 10 ml of THF are added slowly to 2.89 g (0.01 mol) of butyldibromoborane-dimethyl sulfide which has been cooled to 0° C. The Grignard solution is then added dropwise over 30 minutes at the same temperature and, once addition is complete, the mixture is refluxed for 2 h. The mixture is then concentrated in vacuo and the resulting oily residue is dissolved in 80 ml of a 4:1 mixture of methanol and water. Following filtration and treatment of the filtrates with 3.3 g (0,03 mol) of tetramethylammonium chloride, a white solid is precipitated. This precipitate is filtered off, washed with water and dried in vacuo, to give 2.1 g (51% of theory) of the borate, with a melting point of 248–250° C. . The shift δ in $^{11}$B NMR spectrum in $CD_3COCD_3$ is −8.21 ppm.

EXAMPLE 19a

The compound of Example 19a is obtained by a method similar to that described in Example 18b, using the appropriate starting compounds. The structure and the physical data are given in Table 2.

TABLE 2

$$\left[ \begin{array}{c} R_1 \\ | \\ R_4\!-\!B\!-\!R_2 \\ | \\ R_3 \end{array} \right]^{-} X^{+}$$

| Ex. | $R_1$ | $R_2$ | $R_3$ | $R_4$ | $X^+$ | Melting point [° C.] | $^{11}$B-NMR** |
|---|---|---|---|---|---|---|---|
| 1a | Mesityl | Mesityl | Phenyl | Methyl | $N(CH_3)_4$ | 249–250 | −8.71 |
| 1b | Mesityl | Mesityl | Phenyl | Butyl | $N(CH_3)_4$ | 253–254 | −9.93 |
| 2a | Bromo-mesityl | Bromo-mesityl | Phenyl | Methyl | $N(CH_3)_4$ | 205–206 | −8.45 |
| 3a | Dichloro-mesityl | Dichloro-mesityl | Phenyl | Methyl | $N(CH_3)_4$ | 200–201 | −7.81 |
| 3b | Dichloro-mesityl | Dichloro-mesityl | Phenyl | Butyl | $N(CH_3)_4$ | 204–205 | −6.40 |
| 4a | Chloro-mesityl | Chloro-mesityl | Phenyl | Methyl | $N(CH_3)_4$ | 200–203 | −7.84 |
| 4b | Chloro-mesityl | Chloro-mesityl | Phenyl | Butyl | $N(CH_3)_4$ | 208–210 | −7.64 |
| 5a | Mesityl | Mesityl | p-Fluoro-phenyl | Methyl | $N(CH_3)_4$ | 258–260 | −9.86 |
| 5b | Mesityl | Mesityl | p-Fluoro-phenyl | Butyl | $N(CH_3)_4$ | 221–225 | −8.63 |
| 6a | Mesityl | Mesityl | m-Fluoro-phenyl | Methyl | $N(CH_3)_4$ | 249–250 | −10.01 |
| 6b | Mesityl | Mesityl | m-Fluoro-phenyl | Butyl | $N(CH_3)_4$ | 245–246 | −8.42 |
| 7a | Mesityl | Mesityl | 3,4-Di-fluorophenyl | Methyl | $N(CH_3)_4$ | 260–261 | −10.18 |
| 8a | Mesityl | Mesityl | 3,5-Di-fluorophenyl | Methyl | $N(CH_3)_4$ | 244–246 | −9.63 |
| 9a | Mesityl | Mesityl | 3,5-Bis(tri-fluoro-methyl)-phenyl | Methyl | $N(CH_3)_4$ | 254–256 | ++ |
| 9b | Mesityl | Mesityl | 3,5-Bis(tri-fluoro-methyl)-phenyl | Butyl | $N(CH_3)_4$ | 205–206 | −8.54 |
| 10a | Mesityl | Mesityl | 3-Bromo-5-fluorophenyl | Methyl | $N(CH_3)_4$ | 195–200 | ++ |
| 11a | Mesityl | Mesityl | p-Chloro-phenyl | Methyl | $N(CH_3)_4$ | 255–256 | −9.96 |
| 11b | Mesityl | Mesityl | p-Chloro-phenyl | Butyl | $N(CH_3)_4$ | 247–249 | −8.73 |
| 12a | Mesityl | Mesityl | m-Chloro-phenyl | Methyl | $N(CH_3)_4$ | 232–236 | −9.96 |
| 12b | Mesityl | Mesityl | m-Chloro-phenyl | Butyl | $N(CH_3)_4$ | 240–241 | −8.52 |
| 13a | Mesityl | Mesityl | p-Bromo-phenyl | Methyl | $N(CH_3)_4$ | >250 | −10.12 |
| 14a | Chloro-mesityl | Chloro-mesityl | p-Bromo-phenyl | Methyl | $N(CH_3)_4$ | 248–249 | ++ |
| 15a | Mesityl | Mesityl | 2, 5-Di-methyl-4-bromo-phenyl | Methyl | $N(CH_3)_4$ | 240–242 | −9.41 |
| 16a | Mesityl | Mesityl | Mesityl | Methyl | $N(CH_3)_4$ | >230 | −9.94 |
| 17a | p-Chloro-duryl | p-Chloro-duryl | Phenyl | Butyl | $N(CH_3)_4$ | | −7.78 |
| 17b | p-Chloro-duryl | p-Chloro-duryl | Butyl | Methyl | $N(CH_3)_4$ | 164–165 | −8.80 |
| 18a | o-Tolyl | o-Tolyl | o-Tolyl | Methyl | $N(CH_3)_4$ | >250 | −9.55 |
| 18b | o-Tolyl | o-Tolyl | o-Tolyl | Butyl | $N(CH_3)_4$ | 248–250 | −8.21 |
| 19a | o-Methoxy-phenyl | o-Methoxy-phenyl | o-Methoxy-phenyl | Butyl | $N(CH_3)_4$ | ++ | *** |
| 20a | Mesityl | Mesityl | Butyl | Methyl | $N(CH_3)_4$ | 194–195 | *** |
| 21a | Mesityl | Mesityl | $(CH_3)_3Si\text{—}CH_2\text{—}$ | Methyl | $N(CH_3)_4$ | 145–147 | ++ |
| 22a | Mesityl | Mesityl | Phenyl | Phenyl | $N(C_{10}H_{21})_4$ | 182–183 | *** |
| 22b | Mesityl | Mesityl | Phenyl | Phenyl | Cyanine**** | ++ | *** |
| 23a | $(CH_3)_3Si\text{—}CH_2\text{—}$ | $(CH_3)_3Si\text{—}CH_2\text{—}$ | $(CH_3)_3Si\text{—}CH_2\text{—}$ | $(CH_3)_3Si\text{—}CH_2\text{—}$ | $N(CH_3)_4$ | 165–167 | −13.00 |
| 23b | $(CH_3)_3Si\text{—}CH_2\text{—}$ | $(CH_3)_3Si\text{—}CH_2\text{—}$ | $(CH_3)_3Si\text{—}CH_2\text{—}$ | $(CH_3)_3Si\text{—}CH_2\text{—}$ | $N(C_4H_9)_4$ | ++ | *** |
| 23c | $(CH_3)_3Si\text{—}CH_2\text{—}$ | $(CH_3)_3Si\text{—}CH_2\text{—}$ | $(CH_3)_3Si\text{—}CH_2\text{—}$ | $(CH_3)_3Si\text{—}CH_2\text{—}$ | Benzyl-trimethyl-ammonium | ++ | *** |
| 23d | $(CH_3)_3Si\text{—}CH_2\text{—}$ | $(CH_3)_3Si\text{—}CH_2\text{—}$ | $(CH_3)_3Si\text{—}CH_2\text{—}$ | $(CH_3)_3Si\text{—}CH_2\text{—}$ | Benzyl-triethyl ammonium | ++ | *** |
| 23e* | $(CH_3)_3Si\text{—}CH_2\text{—}$ | $(CH_3)_3Si\text{—}CH_2\text{—}$ | $(CH_3)_3Si\text{—}CH_2\text{—}$ | Methyl | $N(CH_3)_4$ | 110–116 | −15.90 −14.34 −13.00 |
| 24a | Chloro-mesityl | Chloro-mesityl | Chloro-mesityl | Methyl | $N(CH_3)_4$ | <230 | −8.72 −8.60 −8.48 |
| 24b | Chloro-mesityl | Chloro-mesityl | Chloro-mesityl | Butyl | $N(CH_3)_4$ | Harz | |
| 25a | Dichloro-mesityl | Dichloro-mesityl | Dichloro-mesityl | Methyl | $N(CH_3)_4$ | 155–158 | −6.98 |
| 26a | m-Tolyl | m-Tolyl | m-Tolyl | Methyl | $N(CH_3)_4$ | 144–148 | *** |

TABLE 2-continued $$\left[\begin{array}{c} R_1 \\ R_4-B-R_2 \\ R_3 \end{array}\right]^- X^+$$

| Ex. | $R_1$ | $R_2$ | $R_3$ | $R_4$ | $X^+$ | Melting point [°C.] | $^{11}$B-NMR** |
|---|---|---|---|---|---|---|---|
| 27a | p-Tolyl | p-Tolyl | p-Tolyl | Methyl | $N(CH_3)_4$ | 161–188 | *** |
| 28a | Mesityl | Mesityl | o-Tolyl | Methyl | $N(CH_3)_4$ | >230 | *** |
| 29a | Mesityl | Mesityl | p-Dimethyl-amino-phenyl | Methyl | $N(CH_3)_4$ | ++ | *** |
| 32a | Mesityl | Mesityl | Mesityl | Methyl | $N(CH_3)_4$ | >230 | −5.46 |
| 33a | Dichloro mesityl | Dichloro mesityl | 4'-Bromo-biphenyl | Methyl | $N(CH_3)_4$ | | |
| 34a*[1] | Mesityl | Mesityl | 9-Phenanthryl | Butyl | $N(CH_3)_4$ | 139–140 | |
| 35a | Mesityl | Mesityl | 1-Naphthyl | Methyl | $N(CH_3)_4$ | 226–227 | |
| 35b | Mesityl | Mesityl | 1-Naphthyl | Butyl | $N(CH_3)_4$ | 200–201 | −7.43 |

*The compound of Example 23e is a 3:10:1 mixture of the compound of Example 23a, tetramethylammonium methyl-tris(trimethylsilylmethyl)borate, and tetramethylammonium dimethylbis(trimethylsilylmethyl) borate
*[1]The preparation of the corresponding borane is described in CA-A-912019
**The $^{11}$B NMR spectra were recorded at 160 MHz in $CD_3COCD_3$ or $CD_3CN$ using $BF_3$-diethyletherate as standard
++ Not determined
*** The $^1$H NMR spectral values are given in Table 3 below
****Cyanine is

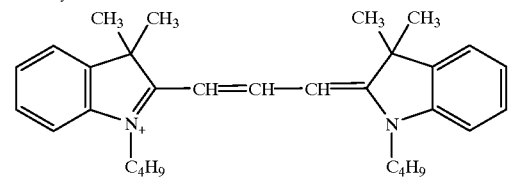

TABLE 2a

| Example | Cation | melting point [°C.] | $^{11}$B-NMR; δ [ppm] |
|---|---|---|---|
| 35c | $^+N(CH_3)_3(n-C_{16}H_{33})$ | 70–72 | −4.65 (Aceton-$d_6$) |
| 35d | (phenyl-piperazinium with N$^+$(CH$_3$)$_2$) | 183–186 | −4.65 (Aceton-$d_6$) |
| 35e | $(Phenyl)_3-\overset{+}{P}-CH_2-\overset{O}{\underset{\|}{C}}-OCH_3$ | 130–131 | −4.66 (Aceton-$d_6$) |
| 35f | $(Phenyl)_3S^+$ | 127–135 | ++ |

++ Not determined

TABLE 3

| Compound | $^1$H NMR(CD$_3$CN), δ [ppm], J[Hz] |
|---|---|
| 19a | 7.06(br s, 3), 6.80(dt, 3, J=7), 6.61–6.54(m, 6), 3.27(s, 9), 3.03(s, 12), 1.27–1.17(m, 2), 1.08(br m, 2), 0.76(t, 3, J=7), 0.71(br m, 2) |
| 20a | 6.33(s, 4), 3.02(s, 12), 2.06(s, 12), 2.05(s, 6), 1.10(m, 2), 0.83(m, 4), 0.71(t, 3, J=7), −0.03(m, 3) |
| 22a | 7.37(br s, 4), 6.80(t, 4, J=7), 6.68(t, 2, J=7), 6.31(s, 4), 3.13(br m, 8), 2.03(s, 6), 1.68(s, 12), 1.54(br m, 8), 1.25 (br m, 56), 0.86(br t, 12, J=7) |
| 22b | 8.45(t, 1, J=14), 7.52–7.39(m, 8), 7.28(m, 4), 6.86 (t, 4, J=7), 6.73(t, 2, J=7), 6.40(s, 4), 6.31(d, 2, J=14), 4.00(br t, 4, J=7), 2.08(s, 6), 1.77(s, 12), 1.77(m, 4), 1.71(s, 12), 1.51–1.40(m, 4), 0.99(t, 6, J=7) |
| 23b | 3.09–3.04(m, 8), 1.64–1.53(m, 8), 1.40–1.28(m, 8), 0.96 (t, 12, J=7), −0.13(s, 36), −0.62(q, 8, J=5) |
| 23c | 7.52–7.47(m, 5), 4.37(s, 2), 2.98(s, 9), −0.13(s, 36), −0.62 (q, 8, J=5) |
| 23d | 7.52–7.46(m, 5), 4.31(s, 2), 3.14(q, 6, J=7), 1.35 (t, 9, J=7), −0.11(s, 36), −0.61(q, 8, J=5) |
| 26a | 7.16(br s, 3), 7.09(br s, 3), 6.81(t, 3, J=7), 6.58(d, 3, J=7), 2.94(s, 12), 2.13(s, 9), 0.25(q, 3, J=3) |
| 27a | 7.12(m, 6), 6.83(d, 6, J=8), 2.87(s, 12), 2.22(s, 9), 0.18(q, 3, J=4) |
| 28a | 6.90(br t, 1), 6.65(br d, 1, J=7), 6.53(t, 1, J=7), 6.41 (t, 1, J=7), 6.27(s, 4), 3.30(s, 12), 2.06(s, 3), 1.95(s, 6), 1.70(s, 12), 0.36(q, 3, J=3) |
| 29a | 7.27(br s, 2), 6.59(br d, 2, J=8), 6.52(s, 4), 3.17(s, 12), 2.88(s, 6), 2.21(s, 6), 1.95(s, 12), 0.48(q, 3, J=3) |

Compound 30a: Methyl(p-trimethylammoniophenyl) dimesityl borate

[Compound of formula I' in which $R_1$ and $R_3$=mesityl, $R_4$=methyl, $R_{2a}$=phenylene and $E^+$=N(CH$_3$)$_3$]

0.4 ml (0.0036 mol) of methyl trifluoromethylsulfonate is added at 0° C. to a stirred suspension of 1.50 g (0.0033 mol) of the compound 29a in 25 ml of dichloromethane. The reaction mixture is allowed to warm to room temperature slowly and is then stirred at this temperature for 3.5 hours. The solvent is removed and the resulting solid is dissolved in ethyl acetate and washed with water. The organic phase is treated with magnesium sulfate, filtered and concentrated, to give 0.35 g (i.e. 27%) of a white solid whose melting point is >230° C. The signal in the $^{11}$B NMR spectrum measured in DMSO-d$_6$, is at −10.38 ppm.

Compound 31 a: Methyl(p-benzyldimethylammoniophenyl) dimesityl borate

[Compound of the formula I in which $R_1$ and $R_3$=mesityl, $R_4$=methyl, $R_{2a}$=phenylene and $E^+$=N(CH$_3$)$_2$(CH$_2$—C$_6$H$_5$)]

Compound 31a is prepared by the same method as compound 30a. However, the methyl trifluoromethylsulfonate is replaced by 2 equivalents of benzyl bromide in acetonitrile.

III. USE EXAMPLES

Example 36

Reactivity test in a clearcoat

A photocurable composition is prepared by mixing the following components:

10.0 g of dipentaerythritol monohydroxypentaacrylat, ®SR399, Sartomer (Craynor, France)
15.0 g of tripropylene glycol diacrylate
15.0 g of N-vinylpyrrolidone, Fluka
10.0 g of trismethylolpropane triacrylate, Degussa
50.0 g of urethane acrylate ®Actilan AJ20, Société Nationale des Poudres et Explosifs 0.3 g of levelling assistant ®Byk 300, Byk-Mallinckrodt.

Portions of this composition are mixed with 0.4% of the borate compound to be tested and with 0.3% of (N,N-dibutyl)dimethylindocarbocyanine chloride*, based on the total quantity of the formulation. All operations are carried out under red lights. The samples to which initiator has been added are applied to a 300 μm aluminium foil. The thickness of the dry film is about 60–70 μm. To this film there is applied a 76 μm thick polyester film, over which a standardized test negative with 21 steps of different optical density (Stouffer wedge) is placed. The sample is covered with a second UV-transparent film and is compressed on a metal plate by means of vacuum. Exposure takes place for 20 seconds using a 4 kW xenon lamp at a distance of 30 cm. Following exposure, the cover films and the mask are removed and the exposed layer is developed in ethanol in an ultrasound bath at 23° C. for 10 seconds. Drying takes place at 40° C in a convection oven for 5 minutes. The sensitivity of the initiator system used is characterized by stating the last wedge step reproduced without tack. The higher the number of steps, the more sensitive the system tested. The results are compiled in Tables 4a–f

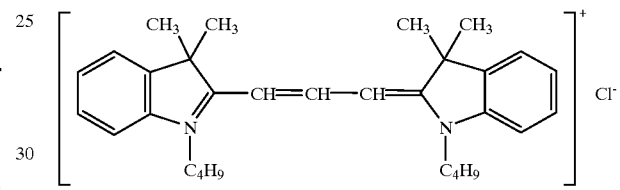

TABLE 4a

| Compound | Number of steps cured |
|---|---|
| 5a | 17 |
| 5b | 21 |
| 6a | 15 |
| 6b | 17 |
| 9b | 15 |
| 11a | 15 |
| 11b | 18 |
| 23a | 18 |
| 23e | 19 |

TABLE 4b

| Compound | Number of steps cured | Bleaching behaviour |
|---|---|---|
| 1a | 18 | b |
| 13a | 17 | b |
| 20a | 18 | — |
| 21a | 17 | — |

*b = bleaches out (visual examination)
— = no bleaching out is observed; however, this does not mean that it does not occur but that it is not noted in the course of visual examination

TABLE 4C

| Compound | Number of steps cured | Bleaching* behaviour |
|---|---|---|
| 18b | 18 | b |

*b = bleaches out (visual examination)

TABLE 4d

| Compound | Number of steps cured |
| --- | --- |
| 19a | 18 |

TABLE 4e

| Compound | Number of steps cured |
| --- | --- |
| 24a | 16 |

TABLE 4f

| Compound from example | Number of steps reproduced after exposure for 20 s |
| --- | --- |
| 25a | 6 |

TABLE 4g

| Compound from example | Number of steps reproduced after exposure for 20 s | Bleaching* behaviour |
| --- | --- | --- |
| 26a | 15 | b |
| 27a | 16 | b |
| 32a (CG 34-0282) | 18 | b |

*b = bleaches out (visual examination)

TABLE 4h

| Compound from example | Number of steps reproduced after exposure for 20 s | Bleaching behaviour |
| --- | --- | --- |
| 28a | 17 | b |
| 30a | 0 | — |
| 31a | 0 | — |

*b = bleaches out (visual examination)
— = no bleaching out is observed; however, this does not mean that it does not occur but that it is not noted in the course of visual examination

Example 37
Photocuring of a monomer-polymer mixture

A photocurable composition is prepared by mixing the following components:

| | |
| --- | --- |
| 37.64 g | of ® Sartomer SR 444, pentaerythritol triacrylat, (Sartomer Company, Westchester) |
| 10.76 g | of ® Cymel 301, Hexamethoxymethylmelamine(American Cyanamid, USA) |
| 47.30 g | ® Carboset 525, thermoplastic polyacrylate containing carboxyl groups (B. F. Goodrich) |
| 4.30 g | Polyvinylpyrrolidone PVP(GAF, USA) |
| 100.00 g | of this composition are mixed with |
| 319,00 g | of methylene chloride and |
| 30,00 g | of methanol. |

Portions of this composition are mixed with 0.4% of a novel borate and with 0.3% of (N,N-dibutyl) dimethylindocarbocyanine chloride, based on the solids content, by stirring at room temperature for one hour. All operations are carried out under red lights. The samples to which initiator has been added are applied to a 300 $\mu$m aluminium foil (10×15 cm). The solvent is removed first of all by drying at room temperature for 5 minutes and then by heating at 60° C. for 15 minutes in a convection oven, giving a dry film thickness of 35 $\mu$m. To this liquid film there is placed a 76 $\mu$m thick polyester film, over which a standardized test negative with 21 steps of different optical density (Stouffer wedge) is applied. The sample is covered with a second UV-transparent film and is compressed on a metal plate by means of vacuum. Exposure takes place for 40 seconds using a 4 kW xenon lamp at a distance of 30 cm. Following exposure, the cover films and the mask are removed and the exposed film is developed with a 1% strength aqueous solution of sodium carbonate in an ultrasound bath for 240 seconds. Drying takes place at 60° C. in a convection oven for 15 minutes. The sensitivity of the initiator system used is characterized by stating the last wedge step reproduced without tack. The higher the number of steps, the more sensitive the system tested. On this scale, an increase by two steps denotes approximately a doubling in the curing rate. The results are stated in Tables 5, 5a and 5b.

TABLE 5

| Compound | Number of steps cured |
| --- | --- |
| 2a | 20 |
| 2b | 19 |
| 3a | 15 |
| 4a | 18 |
| 7a | 18 |
| 8a | 19 |
| 15a | 20 |

TABLE 5a

| Compound | Number of steps cured | Bleaching behaviour* |
| --- | --- | --- |
| 24a | 19 | colour change |

TABLE 5b

| Compound from example | Number of steps reproduced after exposure for 20 s | Bleaching behaviour* |
| --- | --- | --- |
| 25a | 11 | b |

*b = bleaches out (visual examination)
— = no bleaching out is observed; however, this does not mean that it does not occur but that it is not noted in the course of visual examination

TABLE 5c

| Compound from example | Number of steps reproduced after exposure for 20 s | Bleaching behaviour* |
| --- | --- | --- |
| 26a | 18 | b |
| 27a | 16 | b |
| 32a) | 17 | — |

*b = bleaches out (visual examination)
— = no bleaching out is observed; however, this does not mean that it does not occur but that it is not noted in the course of visual examination TABLE 5d

| Compound of example | Number of steps reproduced after exposure for 20 s | Bleaching behaviour* |
|---|---|---|
| 28a | 21 | b |
| 30a | 13 | — |
| 31a | 14 | — |

*b = bleaches out (visual examination)
— = no bleaching out is observed; however, this does not mean that it does not occur but that it is not noted in the course of visual examination Example 38

Reactivity of a dye-borate in a clearcoat 0.3% of a novel dye-borate salt is incorporated into a formulation as in Example 36. Sample preparation, exposure, development and evaluation are likewise similar to those in Example 36. The results are reproduced in Table 6.

TABLE 6

| Compound from Example | Number of steps reproduced |
|---|---|
| 22b | 8 |

Example 39

Reactivity of a dye-borate in a resist formulation 0.3% of a novel dye-borate salt is incorporated into a formulation as in Example 37. Sample preparation, exposure, development and evaluation are likewise similar to those in Example 37. The results are reproduced in Table 7.

TABLE 7

| Compound from Example | Number of steps reproduced |
|---|---|
| 22b | 8 |

Example 40

Reactivity of the borates in combination with electron acceptors in a clearcoat 0.4% of a novel borate salt in combination with 0.3% of Quantacure ITX

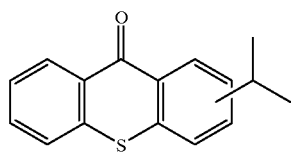

Sample preparation, exposure, development and evaluation are likewise as in Example 36. The results are reproduced in Table 10.

TABLE 10

| Compound from example | Number of steps reproduced |
|---|---|
| 28a | 12 |
| 5a | 11 |
| 1a | 13 |

Example 41

Reactivity of the dye-borate salts in combination with electron acceptors in a clearcoat 0.3% of a novel dye-borate salt in combination with 0.3% of the electron acceptor C

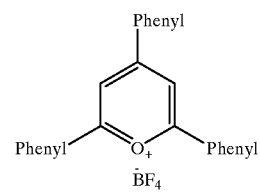

is incorporated into a formulation as in Example 36.

Sample preparation, exposure, development and evaluation are likewise as in Example 36. The results are reproduced in Table 11.

TABLE 11

| Compound for example | Electron acceptor | Number of steps reproduced |
|---|---|---|
| 22b | C | 13 |

Example 42

Reactivity of the dye-borate salts in combination with borates in a clearcoat 0.3% of a novel dye-borate salt in combination with 0.3% of tetramethylammonium n-butyl triphenyl borate is incorporated into a formulation as in Example 36.

Sample preparation, exposure, development and evaluation are likewise as in Example 36. A bleaching of the higher irradiated steps occurs.

What is claimed is:

1. A compound of formula I or I'

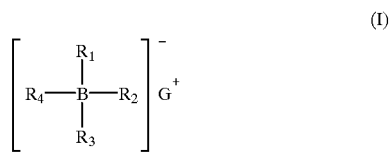

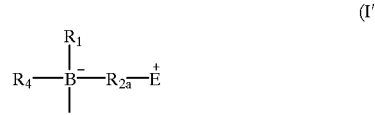

in which
$R_1$ and $R_2$ independently of one another are phenyl or another aromatic hydrocarbon, with or without any heteroatom, which radicals are unsubstituted or are substituted 1–5 times by $C_1$–$C_{20}$alkyl, $C_2$–$C_{20}$alkyl which is interrupted by one or more radicals O, $S(O)_p$ or $NR_5$, or are 4 substituted by $OR_6$, $R_6S(O)_p$, $R_6S(O)_2O$, $R_7R_8N$, $R_6OC(O)$, $R_7R_8NC(O)$, $R_9C(O)$, $R_9R_{10}R_{11}Si$, $R_9R_{10}R_{11}Sn$, $R_{12}R_{13}B$, halogen, $R_9R_{10}P(O)_q$, and/or CN, with the proviso that the phenyl radical or the other aromatic hydrocarbon radicals are substituted in at least one o-position, or the radicals $R_1$ and $R_2$ form bridges to produce structures of the formula II, IIa or IIb

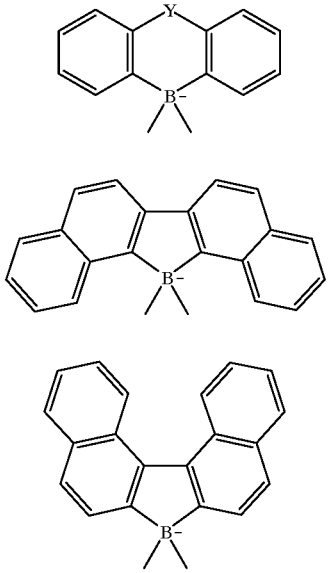

where the aromatic rings in the formulae II, IIa or IIb are unsubstituted or are substituted by $C_1$–$C_{20}$alkyl, $C_2$–$C_{20}$alkyl which is interrupted by one or more radicals O, $S(O)_p$ or $NR_5$ or are substituted by $OR_6$, $R_6S(O)_p$, $R_6S(O)_2O$, $R_7R_8N$, $R_6OC(O)$, $R_7R_8NC(O)$, $R_9C(O)$, $R_9R_{10}R_{11}Si$, $R_9R_{10}R_{11}Sn$, halogen, $R_9R_{10}P(O)_q$ and/or $R_{12}R_{13}B$;

$R_{2a}$ is phenylene or another divalent aromatic hydrocarbon, with or without any heteroatom, which radicals are unsubstituted or are substituted 1–5 times by $C_1$–$C_{20}$alkyl, $C_2$–$C_{20}$alkyl which is interrupted by one or more radicals O, $S(O)_p$ or $NR_5$, or are substituted by $OR_6$, $R_6S(O)_p$, $R_6S(O)_2O$, $R_7R_8N$, $R_6OC(O)$, $R_7R_8NC(O)$, $R_9C(O)$, $R_9R_{10}R_{11}Si$, $R_9R_{10}R_{11}Sn$, $R_{12}R_{13}B$, halogen, $R_9R_{10}P(O)_q$, and/or CN, or $R_{2a}$ is phenyl-$C_1$–$C_6$alkylene;

$R_3$ is phenyl or another aromatic hydrocarbon, with or without any heteroatom, where the phenyl radical or the other aromatic hydrocarbon radicals are unsubstituted or are substituted 1–5 times by $C_1$–$C_{20}$alkyl, $C_2$–$C_{20}$alkyl which is interrupted by one or more radicals O, $S(O)_p$ or $NR_5$, or are substituted by $OR_6$, $R_6S(O)_p$, $R_6S(O)_2O$, $R_7R_8N$, $R_6OC(O)$, $R_7R_8NC(O)$, $R_9C(O)$, $R_9R_{10}R_{11}Si$, $R_9R_{10}R_{11}Sn$, $R_{12}R_{13}B$, halogen, $R_9R_{10}P(O)_q$, and/or CN;

$R_4$ is $C_1$–$C_{20}$alkyl, $C_2$–$C_{20}$alkyl which is interrupted by one or more radicals O, $S(O)_p$ or $NR_5$, or is $C_3$–$C_{12}$cycloalkyl, $C_2$–$C_8$alkenyl, phenyl-$C_1$–$C_6$alkyl or naphthyl-$C_1$–$C_3$alkyl, where the radicals $C_1$–$C_{20}$alkyl, $C_3$–$C_{12}$cycloalkyl, $C_2$–$C_8$alkenyl, phenyl-$C_1$–$C_6$alkyl or naphthyl-$C_1$–$C_3$alkyl are unsubstituted or are substituted by $OR_6$, $R_6S(O)_p$, $R_6S(O)_2O$, $R_7R_8N$, $R_6OC(O)$, $R_7R_8NC(O)$, $R_9R_{10}R_{11}Sn$, $R_{12}R_{13}B$, halogen, $R_9R_{10}P(O)_q$, and/or CN;

E is $R_{14}R_{15}R_{16}P$, $R_6R_{6a}S$ or $R_8R_{8a}R_7N$;

Y is $(CH_2)_n$, CH=CH, C(O), $NR_5$, C, $S(O)_p$ or

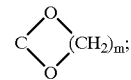

n is 0, 1 or 2;

m is 2 or 3;

p is 0, 1 or 2;

q is 0 or 1;

$R_5$ is hydrogen, $C_1$–$C_{12}$alkyl, phenyl-$C_1$–$C_6$alkyl or phenyl, where the radicals phenyl-$C_1$–$C_6$alkyl or phenyl are unsubstitued or are substituted 1–5 times by $C_1$–$C_6$alkyl, $C_1$–$C_{12}$alkoxy and/or halogen;

$R_6$ and $R_{6a}$ independently of one another are $C_1$–$C_{12}$alkyl, phenyl-$C_1$–$C_6$alkyl or phenyl, where the radicals phenyl-$C_1$–$C_6$alkyl or phenyl are unsubstituted or are substituted 1–5 times by $C_1$–$C_6$alkyl, $C_1$–$C_{12}$alkoxy and/or halogen;

$R_7$, $R_8$ and $R_{8a}$ independently of one another are $C_1$–$C_{12}$alkyl, $C_3$–$C_{12}$cycloalkyl, phenyl-$C_1$–$C_6$alkyl or phenyl where the radicals phenyl-$C_1$–$C_6$alkyl or phenyl are unsubstituted or are substituted 1–5 times by $C_1$–$C_6$alkyl, $C_1$–$C_{12}$alkoxy, $R_6OC(O)$, CN and/or halogen or $R_7$ and $R_8$ together with the N atom to which they are attached, form a 5- or 6-membered ring which may additionally contain O or S atoms;

$R_9$, $R_{10}$ and $R_{11}$ independently of one another are $C_1$–$C_{12}$alkyl, $C_3$–$C_{12}$cycloalkyl, phenyl-$C_1$–$C_6$alkyl or phenyl, where the radicals phenyl-$C_1$–$C_6$alkyl or phenyl are unsubstituted or are substituted 1–5-times by $C_1$–$C_6$alkyl, $C_1$–$C_{12}$alkoxy and/or halogen;

$R_{12}$ and $R_{13}$ independently of one another are $C_1$–$C_{12}$alkyl, $C_3$–$C_{12}$cycloalkyl, phenyl-$C_1$–$C_6$alkyl or phenyl where the radicals phenyl-$C_1$–$C_6$alkyl or phenyl are unsubstituted or are substituted 1–5 times by $C_1$–$C_6$alkyl, $C_1$–$C_{12}$alkoxy and/or halogen, or $R_{12}$ and $R_{13}$, together with the B atom to which they are attached, form a 5- or 6-membered ring;

$R_{14}$, $R_{15}$ and $R_{16}$ independently of one another are $C_1$–$C_{12}$alkyl, $C_2$–$C_{12}$alkenyl, $C_3$–$C_{12}$cycloalkyl, where the radicals $C_1$–$C_{12}$alkyl, $C_2$–$C_{12}$alkenyl, $C_3$–$C_{12}$cycloalkyl are unsubstituted or are substituted by $R_6OCO$ or CN, or $R_{14}$, $R_{15}$ and $R_{16}$ are phenyl-$C_1$–$C_6$alkyl, which is unsubstituted or is substituted one to five times by $C_1$–$C_6$alkyl, $C_1$–$C_{12}$alkoxy or halogen, or are phenyl which is unsubstituted or is substituted one to five times by $C_1$–$C_6$alkyl, $C_1$–$C_{12}$alkoxy or halogen; and G is a radical which is able to form positive ions, with the proviso that, when $R_1$, $R_2$ and $R_3$ are 2,4,6-trimethylphenyl, $R_4$ is not $C_2$–$C_{20}$alkyl or $C_2$–$C_8$alkenyl.

2. A compound according to claim 1, in which $R_1$ and $R_2$ independently of one another are phenyl which is substituted in at least one o-position by $C_1$–$C_6$alkyl, $OR_6$, $R_7R_8N$, $R_9R_{10}R_{11}Si$ and/or halogen, or $R_1$ and $R_2$ are o-terphenyl, naphthyl, binaphthyl, anthracyl, phenanthryl, pyrenyl, quinolyl or isoquinolyl, which radicals are unsubstituted or are substituted by $C_1$–$C_6$alkyl, $OR_6$, $R_7R_8N$, $R_9R_{10}R_{11}Si$ and/or halogen.

3. A compound according to claim 1, in which $R_3$ is phenyl, o-, m- or p-terphenyl, naphthyl, binaphthyl, anthracyl, phenanthryl, pyrenyl, quinolyl or isoquinolyl, which radicals are unsubstituted or are substituted by $C_1$–$C_6$alkyl, $OR_6$, $R_7R_8N$, $R_9R_{10}R_{11}Si$ and/or halogen.

4. A compound according to claim 1, in which $R_4$ is $C_1$–$C_{12}$alkyl, $C_2$–$C_{12}$alkyl, which is interrupted by one or more O or $NR_5$ radicals, or is cyclopentyl, cyclohexyl, $C_2$–$C_6$alkenyl, benzyl or phenylethyl, which radicals are unsubstituted or are substituted by $OR_6$, $R_7R_8N$, $R_9R_{10}R_{11}Si$ and/or halogen.

5. A compound according to claim 1, in which $R_1$ and $R_2$ are identical.

6. A compound according to claim 5, in which $R_1$, $R_2$ and $R_3$ are identical.

7. A compound according to claim 1, in which G is an alkali metal, a quaternary ammonium radical, a dye cation, a transition metal complex cation, a sulfonium, sulfoxonium, phosphonium or iodonium salt or a UV absorber containing a cationic group, or a radical MgX or CaX, in which X is $C_1$–$C_8$alkoxy or halogen.

8. A compound of the formula I or I' according to claim 1, in which $R_1$ and $R_2$ are phenyl which is substituted 1–5 times by $C_1$–$C_4$alkyl, $OR_6$ and/or halogen;

$R_{2a}$ is phenylene;

$R_3$ is phenyl which is unsubstituted or is substituted 1–5 times by $C_1$–$C_4$alkyl, $OR_6$, $R_7R_8N$ and/or halogen;

$R_4$ is unsubstituted $C_1$–$C_4$alkyl;

m is 2 or 3;

E is $R_8R_{8a}$ $R_7N$;

$R_6$ is $C_1$–$C_4$alkyl;

$R_7$, $R_8$ and $R_{8a}$ independently of one another are $C_1$–$C_4$alkyl or benzyl;

$R_9$, $R_{10}$ and $R_{11}$ are $C_1$–$C_4$alkyl and

G is tetra($C_1$–$C_4$alkyl)ammonium or benzyl-tri ($C_1$–$C_4$alkyl)ammonium.

9. A process for the thermal polymerization of compounds containing ethylenically unsaturated double bonds, which comprises adding as polymerization initiator at least one compound of the formula I or I' according to claim 1.

10. A process for the photopolymerization of nonvolatile, monomeric, oligomeric or polymeric compounds containing at least one ethylenically unsaturated double bond, which comprises adding to the abovementioned compounds at least one compound of the formula I or I' according to claim 1 and irradiating the mixture with light from the infrared region through the UV region to a wavelength of 200 nm.

11. A process according to claim 10, wherein the compound of the formula I or I' is employed in combination with at least one coinitiator.

12. A process according to claim 11, wherein the compound of the formula I or I' is employed in combination with another photoinitiator and/or other additives.

13. A process according to claim 10, wherein the compound of the formula I or I' is employed in combination with another photoinitiator and/or other additives.

14. A process according to claim 10, wherein the compound of the formula I according to claim 1 G is a dye radical.

15. A process for producing pigmented and unpigmented paints and varnishes, printing inks, powder coatings, printing plates, adhesives, dental compositions, waveguides, optical switches, colour proofing systems, glass fibre cable coatings, screen printing stencils, resist materials, materials for encapsulating electrical and electronic components, for producing photographical reproductions, for producing composites, for producing magnetic recording materials, for producing three-dimensional objects by stereolithography and as image recording material, which comprises irradiating a composition comprising a nonvolatile, monomeric, oligomeric or polymeric compound containing at least one ethylenically unsaturated double bond and at least one compound of formula I or I' according to claim 1, with light from the infrared region through the UV region to a wavelength of 200 nm.

* * * * *